United States Patent
Miller

(10) Patent No.: US 11,426,290 B2
(45) Date of Patent: Aug. 30, 2022

(54) EXPANDABLE INTERVERTEBRAL IMPLANT, SYSTEM, KIT AND METHOD

(71) Applicant: DePuy Synthes Products, Inc., Raynham, MA (US)

(72) Inventor: William Miller, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 630 days.

(21) Appl. No.: 14/640,264

(22) Filed: Mar. 6, 2015

(65) Prior Publication Data

US 2016/0256291 A1 Sep. 8, 2016

(51) Int. Cl.
*A61F 2/44* (2006.01)
*A61F 2/30* (2006.01)

(52) U.S. Cl.
CPC .... *A61F 2/447* (2013.01); *A61F 2002/30405* (2013.01); *A61F 2002/30579* (2013.01)

(58) Field of Classification Search
CPC . A61F 2/442; A61F 2/447; A61F 2002/30579
See application file for complete search history.

(56) References Cited

U.S. PATENT DOCUMENTS

| | | |
|---|---|---|
| 1,802,560 A | 4/1931 | Kerwin et al. |
| 1,924,695 A * | 8/1933 | Olson ............... F16B 39/26 411/134 |
| 1,965,653 A | 7/1934 | Kennedy |
| 2,077,804 A | 4/1937 | Monroe et al. |
| 2,115,250 A | 4/1938 | Bruson |
| 2,121,193 A | 6/1938 | Hanicke |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Godoy et al. |

(Continued)

FOREIGN PATENT DOCUMENTS

| | | |
|---|---|---|
| AU | 2006279558 A1 | 2/2007 |
| AU | 2005314079 | 10/2012 |

(Continued)

OTHER PUBLICATIONS

U.S. Appl. No. 14/640,220, filed Mar. 6, 2015, Marden.

(Continued)

*Primary Examiner* — Jerrah Edwards
*Assistant Examiner* — Christine L Nelson
(74) *Attorney, Agent, or Firm* — BakerHostetler

(57) ABSTRACT

An implant includes a first plate and a second plate, a first wedge member and a second wedge member spaced from the first wedge member that couple the first and second plates together. The first and second wedge members configured to translate along the first and second plates from a first contracted configuration into a second expanded configuration. The implant includes an actuation member coupled to the first wedge member and the second wedge member. The actuating member defines a flange extending toward the first and second plates. The actuation member configured to move the first and second wedge members from the first contracted configuration into the second expanded configuration so that the first and second plates separate from each other.

21 Claims, 19 Drawing Sheets

(56) References Cited

U.S. PATENT DOCUMENTS

| | | | |
|---|---|---|---|
| 2,381,050 | A | 8/1945 | Hardinge et al. |
| 2,388,056 | A | 10/1945 | Hendricks et al. |
| 2,485,531 | A | 10/1949 | William et al. |
| 2,489,870 | A | 11/1949 | William et al. |
| 2,570,465 | A | 10/1951 | Lundholm et al. |
| 2,677,369 | A | 5/1954 | Knowles et al. |
| 2,706,701 | A | 4/1955 | Hans et al. |
| 2,710,277 | A | 6/1955 | Shelanski et al. |
| 2,826,532 | A | 3/1958 | Hosmer |
| 2,900,305 | A | 8/1959 | Siggia |
| 2,977,315 | A | 3/1961 | Scheib et al. |
| 3,091,237 | A | 5/1963 | Skinner |
| 3,112,743 | A | 12/1963 | Cochran et al. |
| 3,115,804 | A | 12/1963 | Lee et al. |
| 3,228,828 | A | 1/1966 | Romano |
| 3,312,139 | A | 4/1967 | Di et al. |
| 3,486,505 | A | 12/1969 | Morrison et al. |
| 3,489,143 | A | 1/1970 | Halloran et al. |
| 3,648,294 | A | 3/1972 | Shahrestani |
| 3,698,391 | A | 10/1972 | Mahony et al. |
| 3,717,655 | A | 2/1973 | Godefroi et al. |
| 3,760,802 | A | 9/1973 | Fischer et al. |
| 3,800,788 | A | 4/1974 | White |
| 3,805,775 | A | 4/1974 | Fischer et al. |
| 3,811,449 | A | 5/1974 | Gravlee et al. |
| 3,842,825 | A | 10/1974 | Wagner |
| 3,848,601 | A | 11/1974 | Ma et al. |
| 3,855,638 | A | 12/1974 | Pilliar |
| 3,867,728 | A | 2/1975 | Stubstad et al. |
| 3,875,595 | A | 4/1975 | Froning |
| 3,889,665 | A | 6/1975 | Ling et al. |
| 3,964,480 | A | 6/1976 | Froning |
| 3,986,504 | A | 10/1976 | Avila |
| 4,013,071 | A | 3/1977 | Rosenberg |
| 4,052,988 | A | 10/1977 | Doddi et al. |
| 4,091,806 | A | 5/1978 | Aginsky |
| 4,105,034 | A | 8/1978 | Shalaby et al. |
| 4,130,639 | A | 12/1978 | Shalaby et al. |
| 4,140,678 | A | 2/1979 | Shalaby et al. |
| 4,141,087 | A | 2/1979 | Shalaby et al. |
| 4,175,555 | A | 11/1979 | Herbert |
| 4,205,399 | A | 6/1980 | Jamiolkowski et al. |
| 4,236,512 | A | 12/1980 | Aginsky |
| 4,249,435 | A | 2/1981 | Smith et al. |
| 4,262,665 | A | 4/1981 | Roalstad et al. |
| 4,262,676 | A | 4/1981 | Jamshidi |
| 4,274,163 | A | 6/1981 | Malcom et al. |
| 4,275,717 | A | 6/1981 | Bolesky |
| 4,312,337 | A | 1/1982 | Donohue |
| 4,312,353 | A | 1/1982 | Shahbabian |
| 4,313,434 | A | 2/1982 | Segal |
| 4,341,206 | A | 7/1982 | Perrett et al. |
| 4,349,921 | A | 9/1982 | Kuntz |
| 4,350,151 | A | 9/1982 | Scott |
| 4,351,069 | A | 9/1982 | Ballintyn et al. |
| 4,352,883 | A | 10/1982 | Lim |
| 4,369,790 | A | 1/1983 | McCarthy |
| 4,399,814 | A | 8/1983 | Pratt et al. |
| 4,401,112 | A | 8/1983 | Rezaian |
| 4,401,433 | A | 8/1983 | Luther |
| 4,409,974 | A | 10/1983 | Freedland |
| 4,440,921 | A | 4/1984 | Allcock et al. |
| 4,449,532 | A | 5/1984 | Storz |
| 4,451,256 | A | 5/1984 | Weikl et al. |
| 4,456,005 | A | 6/1984 | Lichty |
| 4,462,394 | A | 7/1984 | Jacobs |
| 4,463,753 | A | 8/1984 | Gustilo |
| 4,466,435 | A | 8/1984 | Murray |
| 4,467,479 | A | 8/1984 | Brody |
| 4,488,543 | A | 12/1984 | Tornier |
| 4,488,549 | A | 12/1984 | Lee et al. |
| 4,494,535 | A | 1/1985 | Haig |
| 4,495,174 | A | 1/1985 | Allcock et al. |
| 4,532,660 | A | 8/1985 | Field |
| 4,537,185 | A | 8/1985 | Stednitz |
| 4,538,612 | A | 9/1985 | Patrick, Jr. |
| 4,542,539 | A | 9/1985 | Rowe et al. |
| 4,545,374 | A | 10/1985 | Jacobson |
| 4,562,598 | A | 1/1986 | Kranz |
| 4,573,448 | A | 3/1986 | Kambin |
| 4,595,006 | A | 6/1986 | Burke et al. |
| 4,601,710 | A | 7/1986 | Moll |
| 4,625,722 | A | 12/1986 | Murray |
| 4,625,725 | A | 12/1986 | Davison et al. |
| 4,627,434 | A | 12/1986 | Murray |
| 4,628,945 | A | 12/1986 | Johnson, Jr. |
| 4,629,450 | A | 12/1986 | Suzuki et al. |
| 4,630,616 | A | 12/1986 | Tretinyak |
| 4,632,101 | A | 12/1986 | Freedland |
| 4,640,271 | A | 2/1987 | Lower |
| 4,641,640 | A | 2/1987 | Griggs |
| 4,645,503 | A | 2/1987 | Lin et al. |
| 4,646,741 | A | 3/1987 | Smith |
| 4,651,717 | A | 3/1987 | Jakubczak |
| 4,653,489 | A | 3/1987 | Tronzo |
| 4,665,906 | A | 5/1987 | Jervis |
| 4,667,663 | A | 5/1987 | Miyata |
| 4,686,973 | A | 8/1987 | Frisch |
| 4,686,984 | A | 8/1987 | Bonnet |
| 4,688,561 | A | 8/1987 | Reese |
| 4,697,584 | A | 10/1987 | Haynes |
| 4,706,670 | A | 11/1987 | Andersen et al. |
| 4,714,469 | A | 12/1987 | Kenna |
| 4,714,478 | A | 12/1987 | Fischer |
| 4,721,103 | A | 1/1988 | Freedland |
| 4,723,544 | A | 2/1988 | Moore et al. |
| 4,743,256 | A | 5/1988 | Brantigan |
| 4,743,257 | A | 5/1988 | Tormala et al. |
| 4,759,766 | A | 7/1988 | Buettner-Janz et al. |
| 4,760,843 | A | 8/1988 | Fischer et al. |
| 4,772,287 | A | 9/1988 | Ray et al. |
| 4,790,304 | A | 12/1988 | Rosenberg |
| 4,790,817 | A | 12/1988 | Luther |
| 4,796,612 | A | 1/1989 | Reese |
| 4,802,479 | A | 2/1989 | Haber et al. |
| 4,815,909 | A | 3/1989 | Simons |
| 4,827,917 | A | 5/1989 | Brumfield |
| 4,834,069 | A | 5/1989 | Umeda |
| 4,834,757 | A | 5/1989 | Brantigan |
| 4,838,282 | A | 6/1989 | Strasser et al. |
| 4,858,601 | A | 8/1989 | Glisson |
| 4,862,891 | A | 9/1989 | Smith |
| 4,863,476 | A | 9/1989 | Shepperd |
| 4,870,153 | A | 9/1989 | Matzner et al. |
| 4,871,366 | A | 10/1989 | von Recum et al. |
| 4,873,976 | A | 10/1989 | Schreiber |
| 4,878,915 | A | 11/1989 | Brantigan |
| 4,880,622 | A | 11/1989 | Allcock et al. |
| 4,888,022 | A | 12/1989 | Huebsch |
| 4,888,024 | A | 12/1989 | Powlan |
| 4,889,119 | A | 12/1989 | Jamiolkowski et al. |
| 4,892,550 | A | 1/1990 | Huebsch |
| 4,896,662 | A | 1/1990 | Noble |
| 4,898,186 | A | 2/1990 | Ikada et al. |
| 4,898,577 | A | 2/1990 | Badger et al. |
| 4,903,692 | A | 2/1990 | Reese |
| 4,904,261 | A | 2/1990 | Dove et al. |
| 4,911,718 | A | 3/1990 | Lee et al. |
| 4,917,554 | A | 4/1990 | Bronn |
| 4,932,969 | A | 6/1990 | Frey et al. |
| 4,940,467 | A | 7/1990 | Tronzo |
| 4,941,466 | A | 7/1990 | Romano |
| 4,946,378 | A | 8/1990 | Hirayama et al. |
| 4,959,064 | A | 9/1990 | Engelhardt |
| 4,961,740 | A | 10/1990 | Ray et al. |
| 4,963,144 | A | 10/1990 | Huene |
| 4,966,587 | A | 10/1990 | Baumgart |
| 4,968,317 | A | 11/1990 | Tormala et al. |
| 4,969,888 | A | 11/1990 | Scholten et al. |
| 4,978,334 | A | 12/1990 | Toye et al. |
| 4,978,349 | A | 12/1990 | Frigg |
| 4,981,482 | A | 1/1991 | Ichikawa |
| 4,988,351 | A | 1/1991 | Paulos et al. |
| 4,994,027 | A | 2/1991 | Farrell |

(56) References Cited

U.S. PATENT DOCUMENTS

| | | |
|---|---|---|
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Steffee |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muhling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul et al. |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buttner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka et al. |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach, Jr. et al. |

(56) References Cited

U.S. PATENT DOCUMENTS

| | | |
|---|---|---|
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | de Graaf et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble et al. |
| 5,562,736 A | 10/1996 | Ray et al. |
| 5,562,738 A | 10/1996 | Boyd et al. |
| 5,564,926 A | 10/1996 | Brånemark |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach, III et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |
| 5,788,703 A | 8/1998 | Mittelmeier et al. |
| 5,792,044 A | 8/1998 | Foley et al. |
| 5,800,549 A | 9/1998 | Bao et al. |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |

(56) References Cited

U.S. PATENT DOCUMENTS

| | | |
|---|---|---|
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Tienboon |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao et al. |
| 5,976,187 A | 11/1999 | Richelsoph |
| 5,980,522 A | 11/1999 | Koros et al. |
| 5,984,927 A | 11/1999 | Wenstrom, Jr. et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Tormala et al. |
| 6,012,494 A | 1/2000 | Balazs |
| 6,015,410 A | 1/2000 | Toermaelae et al. |
| 6,015,436 A | 1/2000 | Helmut |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li |
| 6,039,763 A | 3/2000 | Shelokov |
| 6,045,552 A | 4/2000 | Zucherman et al. |
| 6,045,579 A | 4/2000 | Hochshuler |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,158 A | 6/2000 | Lin |
| 6,080,193 A | 6/2000 | Hochshuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |

(56) References Cited

U.S. PATENT DOCUMENTS

| | | |
|---|---|---|
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Tormala et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul et al. |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |

(56) References Cited

U.S. PATENT DOCUMENTS

| | | |
|---|---|---|
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul et al. |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | von Hoffmann et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Taylor |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Kraus |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Viart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Tormala et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |

(56) References Cited

U.S. PATENT DOCUMENTS

| | | |
|---|---|---|
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm, Jr. et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum et al. |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B1 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | von Hoffmann et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zucherman et al. |
| 6,905,512 B2 | 6/2005 | Paes et al. |
| 6,908,465 B2 | 6/2005 | von Hoffmann et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg et al. |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |

(56) References Cited

U.S. PATENT DOCUMENTS

| | | |
|---|---|---|
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le Couedic et al. |
| 7,241,297 B2 | 7/2007 | Shaolian et al. |
| 7,244,273 B2 | 7/2007 | Pedersen et al. |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,306,628 B2 | 12/2007 | Zucherman et al. |
| 7,309,357 B2 | 12/2007 | Kim |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 3/2009 | Rogers |
| 7,520,888 B2 | 4/2009 | Trieu |
| 7,547,317 B2 | 6/2009 | Cragg |
| 7,556,629 B2 | 7/2009 | von Hoffmann et al. |
| 7,556,651 B2 | 7/2009 | Humphreys et al. |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,266 B2 | 2/2010 | Izawa et al. |
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,691,120 B2 | 4/2010 | Shluzas et al. |
| 7,691,147 B2 | 4/2010 | Gutlin et al. |
| 7,699,878 B2 | 4/2010 | Pavlov et al. |
| 7,703,727 B2 | 4/2010 | Selness |
| 7,704,280 B2 | 4/2010 | Lechmann et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Assell et al. |
| 7,763,028 B2 | 7/2010 | Lim et al. |
| 7,763,038 B2 | 7/2010 | O'Brien |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |

(56) References Cited

U.S. PATENT DOCUMENTS

| | | |
|---|---|---|
| 7,799,080 B2 | 9/2010 | Doty |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowtiz et al. |
| 7,857,832 B2 | 12/2010 | Culbert et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,118,871 B2 | 2/2012 | Gordon et al. |
| 8,128,700 B2 | 3/2012 | Delurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |
| 8,377,098 B2 | 2/2013 | Landry et al. |
| 8,377,133 B2 | 2/2013 | Yuan et al. |
| 8,382,842 B2 | 2/2013 | Greenhalgh et al. |
| 8,394,129 B2 | 3/2013 | Morgenstern Lopez et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller |
| 8,454,698 B2 | 6/2013 | De et al. |
| 8,465,524 B2 | 6/2013 | Siegal |
| 8,470,043 B2 | 6/2013 | Schaller et al. |
| 8,480,715 B2 | 7/2013 | Gray |
| 8,480,742 B2 | 7/2013 | Pisharodi |
| 8,480,748 B2 | 7/2013 | Poulos |
| 8,486,109 B2 | 7/2013 | Siegal |
| 8,486,148 B2 | 7/2013 | Butler et al. |
| 8,491,591 B2 | 7/2013 | Fuerderer |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Morgenstern et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim |

(56) References Cited

U.S. PATENT DOCUMENTS

| | | |
|---|---|---|
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern Lopez et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McClellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum et al. |
| 8,709,088 B2 | 4/2014 | Kleiner et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern Lopez et al. |
| 8,852,243 B2 | 10/2014 | Morgenstern Lopez et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum |
| 8,936,641 B2 | 1/2015 | Cain |
| 8,940,049 B1 | 1/2015 | Jimenez et al. |
| 8,940,050 B2 | 1/2015 | Laurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,929 B2 | 3/2015 | Schaller |
| 8,986,387 B1 | 3/2015 | To et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,768 B2 | 5/2015 | Voellmicke |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,091,488 B2 | 8/2015 | Malandain |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | Mclean et al. |
| 9,237,956 B1 | 1/2016 | Jensen |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,282,979 B2 | 3/2016 | O'Neil et al. |
| 9,283,092 B2 | 3/2016 | Siegal et al. |
| 9,295,562 B2 | 3/2016 | Lechmann et al. |
| 9,314,348 B2 | 4/2016 | Emstad |
| 9,326,866 B2 | 5/2016 | Schaller et al. |
| 9,333,091 B2 | 5/2016 | Dimauro |
| 9,387,087 B2 | 7/2016 | Tyber |
| 9,402,732 B2 | 8/2016 | Gabelberger |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,936 B2 | 8/2016 | Miller et al. |
| 9,433,510 B2 | 9/2016 | Lechmann et al. |
| 9,439,776 B2 | 9/2016 | Dimauro et al. |
| 9,439,777 B2 | 9/2016 | Dimauro |
| 9,445,825 B2 | 9/2016 | Belaney et al. |
| 9,445,918 B1 | 9/2016 | Lin et al. |
| 9,463,099 B2 | 10/2016 | Levy et al. |
| 9,474,623 B2 | 10/2016 | Cain |
| 9,510,954 B2 | 12/2016 | Glerum et al. |
| 9,532,884 B2 | 1/2017 | Siegal et al. |
| 9,566,167 B2 | 2/2017 | Barrus et al. |
| 9,579,215 B2 | 2/2017 | Suedkamp et al. |
| 9,592,129 B2 | 3/2017 | Slivka et al. |
| 9,597,197 B2 | 3/2017 | Lechmann et al. |
| 9,662,223 B2 | 5/2017 | Matthis et al. |
| 9,662,224 B2 | 5/2017 | Weiman et al. |
| 9,675,470 B2 | 6/2017 | Packer et al. |
| 9,724,207 B2 | 8/2017 | Dimauro et al. |
| 9,730,803 B2 | 8/2017 | Dimauro et al. |
| 9,750,552 B2 | 9/2017 | Stephan et al. |
| 9,750,618 B1 | 9/2017 | Daffinson et al. |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | Dimauro et al. |
| 9,801,734 B1 | 10/2017 | Stein et al. |
| 9,808,351 B2 | 11/2017 | Kelly et al. |
| 9,808,353 B2 | 11/2017 | Suddaby et al. |
| 9,814,589 B2 | 11/2017 | Dimauro |
| 9,814,590 B2 | 11/2017 | Serhan et al. |
| 9,839,528 B2 | 12/2017 | Weiman et al. |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,907,670 B2 | 3/2018 | Deridder et al. |
| 9,924,978 B2 | 3/2018 | Thommen et al. |
| 9,925,060 B2 | 3/2018 | Dimauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,974,664 B2 | 5/2018 | Emerick et al. |
| 9,980,823 B2 | 5/2018 | Matthis et al. |
| 9,993,350 B2 | 6/2018 | Cain |

(56) References Cited

U.S. PATENT DOCUMENTS

| | | |
|---|---|---|
| 10,004,607 B2 | 6/2018 | Weiman et al. |
| 10,058,433 B2 | 8/2018 | Lechmann et al. |
| 10,085,843 B2 | 10/2018 | Dimauro |
| 10,092,417 B2 | 10/2018 | Weiman et al. |
| 10,143,569 B2 | 12/2018 | Weiman et al. |
| 10,219,915 B1 | 3/2019 | Stein |
| 10,238,500 B2 | 3/2019 | Rogers et al. |
| 10,265,191 B2 | 4/2019 | Lim et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,398,566 B2 | 9/2019 | Olmos et al. |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,426,632 B2 | 10/2019 | Butler et al. |
| 10,433,971 B2 | 10/2019 | Dimauro et al. |
| 10,433,974 B2 | 10/2019 | O'Neil |
| 10,433,977 B2 | 10/2019 | Lechmann et al. |
| 10,449,056 B2 | 10/2019 | Cain |
| 10,449,058 B2 | 10/2019 | Lechmann et al. |
| 10,492,918 B2 | 12/2019 | Dimauro |
| 10,492,924 B2 | 12/2019 | Stein et al. |
| 10,512,489 B2 | 12/2019 | Serhan et al. |
| 10,548,741 B2 | 2/2020 | Suedkamp et al. |
| 10,555,817 B2 | 2/2020 | Dimauro et al. |
| 10,575,959 B2 | 3/2020 | Dimauro et al. |
| 10,583,013 B2 | 3/2020 | Dimauro et al. |
| 10,583,015 B2 | 3/2020 | Olmos et al. |
| 10,639,164 B2 | 5/2020 | Dimauro et al. |
| 10,639,166 B2 | 5/2020 | Weiman et al. |
| 10,682,241 B2 | 6/2020 | Glerum et al. |
| 10,743,914 B2 | 8/2020 | Lopez et al. |
| 10,758,371 B2 | 9/2020 | Hessler et al. |
| 10,842,644 B2 | 11/2020 | Weiman et al. |
| 10,888,433 B2 | 1/2021 | Frasier et al. |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0016775 A1 | 8/2001 | Scarborough et al. |
| 2001/0027320 A1 | 10/2001 | Sasso |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045942 A1 | 4/2002 | Ham |
| 2002/0055740 A1 | 5/2002 | Lieberman |
| 2002/0055781 A1 | 5/2002 | Sazy |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0072801 A1 | 6/2002 | Michelson |
| 2002/0077700 A1 | 6/2002 | Varga et al. |
| 2002/0077701 A1 | 6/2002 | Kuslich |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128715 A1 | 9/2002 | Bryan et al. |
| 2002/0128716 A1 | 9/2002 | Cohen et al. |
| 2002/0138078 A1 | 9/2002 | Chappuis |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | von Hoffmann et al. |
| 2002/0151895 A1 | 10/2002 | Soboleski et al. |
| 2002/0151976 A1 | 10/2002 | Foley et al. |
| 2002/0161444 A1 | 10/2002 | Choi |
| 2002/0165550 A1 | 11/2002 | Frey et al. |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173841 A1 | 11/2002 | Ortiz et al. |
| 2002/0173851 A1 | 11/2002 | McKay |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014113 A1 | 1/2003 | Ralph et al. |
| 2003/0014116 A1 | 1/2003 | Ralph et al. |
| 2003/0023305 A1 | 1/2003 | McKay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0050644 A1 | 3/2003 | Boucher et al. |
| 2003/0063582 A1 | 4/2003 | Culbert |
| 2003/0065330 A1 | 4/2003 | Zucherman et al. |
| 2003/0065396 A1 | 4/2003 | Michelson |
| 2003/0069582 A1 | 4/2003 | Culbert et al. |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec |
| 2003/0135275 A1 | 7/2003 | Garcia |
| 2003/0139648 A1 | 7/2003 | Foley et al. |
| 2003/0139812 A1 | 7/2003 | Garcia |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0204261 A1 | 10/2003 | Eisermann |
| 2003/0208122 A1 | 11/2003 | Melkent et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010263 A1 | 1/2004 | Boucher et al. |
| 2004/0010318 A1 | 1/2004 | Ferree |

(56) References Cited

U.S. PATENT DOCUMENTS

| | | |
|---|---|---|
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034429 A1 | 2/2004 | Lambrecht et al. |
| 2004/0049190 A1 | 3/2004 | Biedermann et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059337 A1 | 3/2004 | Hanson et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0068269 A1 | 4/2004 | Bonati et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106925 A1 | 6/2004 | Culbert |
| 2004/0106940 A1 | 6/2004 | Shaolian et al. |
| 2004/0116997 A1 | 6/2004 | Taylor et al. |
| 2004/0117022 A1 | 6/2004 | Marnay et al. |
| 2004/0059339 A1 | 7/2004 | Roehm, III et al. |
| 2004/0127906 A1 | 7/2004 | Culbert et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Fraser et al. |
| 2004/0193277 A1 | 9/2004 | Long et al. |
| 2004/0199162 A1 | 10/2004 | von Hoffmann et al. |
| 2004/0210231 A1 | 10/2004 | Boucher et al. |
| 2004/0210310 A1 | 10/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro |
| 2004/0243229 A1 | 12/2004 | Vidlund et al. |
| 2004/0243239 A1 | 12/2004 | Taylor |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Fallin et al. |
| 2005/0090833 A1 | 4/2005 | Di Poto |
| 2005/0090852 A1 | 4/2005 | Layne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 | 5/2005 | Branch |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Turri |
| 2005/0119657 A1 | 6/2005 | Goldsmith |

(56) References Cited

U.S. PATENT DOCUMENTS

| | | |
|---|---|---|
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131406 A1 | 6/2005 | Reiley et al. |
| 2005/0131409 A1 | 6/2005 | Chervitz et al. |
| 2005/0131411 A1 | 6/2005 | Culbert et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | von Hoffmann et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0149022 A1 | 7/2005 | Shaolian et al. |
| 2005/0149030 A1 | 7/2005 | Serhan |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165420 A1 | 7/2005 | Cha |
| 2005/0165484 A1 | 7/2005 | Ferree |
| 2005/0165485 A1 | 7/2005 | Trieu |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Culbert |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | von Hoffmann et al. |
| 2005/0251149 A1 | 11/2005 | Wenz |
| 2005/0251260 A1 | 11/2005 | Gerber et al. |
| 2005/0256525 A1 | 11/2005 | Warren et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde |
| 2005/0278029 A1 | 12/2005 | Trieu |
| 2005/0283238 A1 | 12/2005 | Reiley |
| 2005/0287071 A1 | 12/2005 | Wenz |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0032621 A1 | 2/2006 | Martin et al. |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |

(56) References Cited

U.S. PATENT DOCUMENTS

| | | |
|---|---|---|
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | DiNello et al. |
| 2006/0136064 A1 | 6/2006 | Sherman |
| 2006/0142759 A1 | 6/2006 | Arnin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247771 A1 | 11/2006 | Peterman et al. |
| 2006/0247781 A1 | 11/2006 | Francis |
| 2006/0253120 A1 | 11/2006 | Anderson et al. |
| 2006/0253201 A1 | 11/2006 | McLuen |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Boyer, II et al. |
| 2006/0282167 A1 | 12/2006 | Lambrecht et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010824 A1 | 1/2007 | Malandain et al. |
| 2007/0010826 A1 | 1/2007 | Rhoda |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055272 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |

(56) References Cited

U.S. PATENT DOCUMENTS

| | | |
|---|---|---|
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Trieu |
| 2007/0233083 A1 | 10/2007 | Abdou |
| 2007/0233089 A1 | 10/2007 | DiPoto et al. |
| 2007/0233130 A1 | 10/2007 | Suddaby |
| 2007/0233244 A1 | 10/2007 | Lopez et al. |
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Trieu et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | de Villiers et al. |
| 2007/0288091 A1 | 12/2007 | Braddock et al. |
| 2007/0299521 A1 | 12/2007 | Glenn |
| 2008/0009877 A1 | 1/2008 | Sankaran et al. |
| 2008/0015694 A1 | 1/2008 | Tribus |
| 2008/0015701 A1 | 1/2008 | Garcia et al. |
| 2008/0021476 A1 | 1/2008 | Kirschman |
| 2008/0021556 A1 | 1/2008 | Edie |
| 2008/0021557 A1 | 1/2008 | Trieu |
| 2008/0021558 A1 | 1/2008 | Thramann |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Link et al. |
| 2008/0033440 A1 | 2/2008 | Moskowitz et al. |
| 2008/0045966 A1 | 2/2008 | Buttermann et al. |
| 2008/0051890 A1 | 2/2008 | Waugh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097454 A1 | 4/2008 | Deridder et al. |
| 2008/0097611 A1 | 4/2008 | Mastrorio et al. |
| 2008/0103601 A1 | 5/2008 | Biro et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0132934 A1 | 6/2008 | Reilly |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147129 A1 | 6/2008 | Biedermann et al. |
| 2008/0147193 A1 | 6/2008 | Matthis et al. |
| 2008/0154379 A1 | 6/2008 | Steiner et al. |
| 2008/0161927 A1 | 7/2008 | Savage |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208344 A1 | 8/2008 | Kilpela et al. |
| 2008/0221586 A1 | 9/2008 | Garcia-Bengochea et al. |
| 2008/0221687 A1 | 9/2008 | Thomas |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | von Hoffmann et al. |
| 2009/0069895 A1 | 3/2009 | Gittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105745 A1 | 4/2009 | Culbert |
| 2009/0112217 A1 | 4/2009 | Hester |

(56) References Cited

U.S. PATENT DOCUMENTS

| | | |
|---|---|---|
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0192614 A1 | 7/2009 | Beger et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez et al. |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van Den Meersschaut et al. |
| 2010/0042218 A1 | 2/2010 | Nebosky et al. |
| 2010/0049324 A1 | 2/2010 | Valdevit et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | McCormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0234956 A1 | 9/2010 | Attia et al. |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0274358 A1 | 10/2010 | Mueller et al. |
| 2010/0286777 A1 | 11/2010 | Errico et al. |
| 2010/0286783 A1 | 11/2010 | Lechmann et al. |
| 2010/0292700 A1 | 11/2010 | Ries |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0035011 A1 | 2/2011 | Cain |
| 2011/0040332 A1 | 2/2011 | Culbert et al. |
| 2011/0046674 A1 | 2/2011 | Calvosa et al. |
| 2011/0054538 A1 | 3/2011 | Zehavi et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130835 A1 | 6/2011 | Ashley et al. |
| 2011/0130838 A1 | 6/2011 | Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160866 A1 | 6/2011 | Laurence et al. |
| 2011/0172716 A1 | 7/2011 | Glerum |
| 2011/0172774 A1 | 7/2011 | Varela |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0270401 A1 | 11/2011 | Mckay |
| 2011/0276142 A1 | 11/2011 | Niemiec et al. |
| 2011/0282453 A1 | 11/2011 | Greenhalgh et al. |
| 2011/0282459 A1 | 11/2011 | McClellan et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0319899 A1 | 12/2011 | O'Neil et al. |
| 2011/0319998 A1 | 12/2011 | O'Neil et al. |
| 2011/0320000 A1 | 12/2011 | O'Neil et al. |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029639 A1 | 2/2012 | Blackwell et al. |
| 2012/0035730 A1 | 2/2012 | Spann |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191204 A1 | 7/2012 | Bae et al. |
| 2012/0197299 A1 | 8/2012 | Fabian, Jr. |

(56) References Cited

U.S. PATENT DOCUMENTS

| | | |
|---|---|---|
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern Lopez et al. |
| 2012/0253395 A1 | 10/2012 | Linares |
| 2012/0253406 A1 | 10/2012 | Bae et al. |
| 2012/0265309 A1 | 10/2012 | Glerum et al. |
| 2012/0277795 A1 | 11/2012 | von Hoffmann et al. |
| 2012/0277869 A1 | 11/2012 | Siccardi et al. |
| 2012/0277877 A1 | 11/2012 | Smith et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323327 A1 | 12/2012 | Mcafee |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0006362 A1 | 1/2013 | Biedermann et al. |
| 2013/0023937 A1 | 1/2013 | Biedermann et al. |
| 2013/0023993 A1* | 1/2013 | Weiman .................. A61F 2/442  623/17.16 |
| 2013/0023994 A1 | 1/2013 | Glerum |
| 2013/0030536 A1 | 1/2013 | Rhoda et al. |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085572 A1 | 4/2013 | Glerum et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1 | 6/2013 | Siegal et al. |
| 2013/0150906 A1 | 6/2013 | Kerboul et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0197647 A1 | 8/2013 | Wolters et al. |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0274883 A1 | 10/2013 | McLuen et al. |
| 2013/0310937 A1 | 11/2013 | Luiz |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0025169 A1 | 1/2014 | Lechmann et al. |
| 2014/0039622 A1 | 2/2014 | Glerum et al. |
| 2014/0039626 A1 | 2/2014 | Dale |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1 | 4/2014 | Glerum et al. |
| 2014/0094917 A1 | 4/2014 | Salerni |
| 2014/0100662 A1 | 4/2014 | Patterson et al. |
| 2014/0107790 A1 | 4/2014 | Combrowski |
| 2014/0114414 A1 | 4/2014 | Abdou et al. |
| 2014/0114423 A1 | 4/2014 | Suedkamp et al. |
| 2014/0121774 A1 | 5/2014 | Glerum et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0148904 A1 | 5/2014 | Robinson |
| 2014/0163682 A1 | 6/2014 | Lott et al. |
| 2014/0163683 A1 | 6/2014 | Seifert et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0236296 A1* | 8/2014 | Wagner .................. A61F 2/447  623/17.15 |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277473 A1 | 9/2014 | Perrow |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0277507 A1 | 9/2014 | Baynham |
| 2014/0296983 A1 | 10/2014 | Fauth et al. |
| 2014/0303731 A1 | 10/2014 | Glerum et al. |
| 2014/0303732 A1 | 10/2014 | Rhoda et al. |
| 2014/0324171 A1 | 10/2014 | Glerum et al. |
| 2014/0336764 A1 | 11/2014 | Masson et al. |
| 2014/0343678 A1 | 11/2014 | Suddaby et al. |
| 2015/0012097 A1 | 1/2015 | Ibarra et al. |
| 2015/0012098 A1* | 1/2015 | Eastlack .................. A61F 2/447  623/17.15 |
| 2015/0045894 A1 | 2/2015 | Hawkins et al. |
| 2015/0057755 A1 | 2/2015 | Suddaby et al. |
| 2015/0066145 A1 | 3/2015 | Rogers et al. |
| 2015/0088256 A1 | 3/2015 | Ballard |
| 2015/0094610 A1 | 4/2015 | Morgenstern Lopez et al. |
| 2015/0094812 A1 | 4/2015 | Marden et al. |
| 2015/0094813 A1 | 4/2015 | Lechmann et al. |
| 2015/0094814 A1 | 4/2015 | Emerick et al. |
| 2015/0100128 A1 | 4/2015 | Glerum et al. |
| 2015/0112398 A1 | 4/2015 | Morgenstern Lopez et al. |
| 2015/0112437 A1 | 4/2015 | Davis et al. |
| 2015/0112438 A1 | 4/2015 | McLean |
| 2015/0173916 A1 | 6/2015 | Cain et al. |
| 2015/0182347 A1 | 7/2015 | Robinson |
| 2015/0190242 A1 | 7/2015 | Blain et al. |
| 2015/0196400 A1 | 7/2015 | Dace |
| 2015/0216671 A1 | 8/2015 | Cain et al. |
| 2015/0216672 A1 | 8/2015 | Cain et al. |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | Mclean |
| 2015/0272743 A1 | 10/2015 | Jimenez et al. |
| 2015/0305881 A1 | 10/2015 | Bal et al. |

(56) References Cited

U.S. PATENT DOCUMENTS

| | | |
|---|---|---|
| 2015/0320571 A1 | 11/2015 | Lechmann et al. |
| 2016/0016309 A1 | 1/2016 | Swift et al. |
| 2016/0022438 A1 | 1/2016 | Lamborne et al. |
| 2016/0038301 A1 | 2/2016 | Wickham |
| 2016/0045333 A1 | 2/2016 | Baynham |
| 2016/0051373 A1 | 2/2016 | Faulhaber |
| 2016/0051374 A1 | 2/2016 | Faulhaber |
| 2016/0067055 A1 | 3/2016 | Hawkins et al. |
| 2016/0081814 A1 | 3/2016 | Baynham |
| 2016/0089247 A1 | 3/2016 | Nichols et al. |
| 2016/0317317 A1 | 3/2016 | Marchek et al. |
| 2016/0100954 A1 | 4/2016 | Rumi et al. |
| 2016/0106551 A1 | 4/2016 | Grimberg et al. |
| 2016/0113776 A1 | 4/2016 | Capote |
| 2016/0120662 A1 | 5/2016 | Schaller |
| 2016/0128843 A1 | 5/2016 | Tsau et al. |
| 2016/0199195 A1 | 7/2016 | Hauck et al. |
| 2016/0199196 A1 | 7/2016 | Serhan et al. |
| 2016/0228258 A1 | 8/2016 | Schaller et al. |
| 2016/0235455 A1 | 8/2016 | Wahl |
| 2016/0242929 A1 | 8/2016 | Voellmicke et al. |
| 2016/0317714 A1 | 11/2016 | Dimauro et al. |
| 2016/0331546 A1 | 11/2016 | Lechmann et al. |
| 2016/0367265 A1 | 12/2016 | Morgenstern Lopez |
| 2017/0000622 A1 | 1/2017 | Thommen et al. |
| 2017/0071756 A1 | 3/2017 | Slivka et al. |
| 2017/0100255 A1 | 4/2017 | Hleihil et al. |
| 2017/0119542 A1 | 5/2017 | Logan et al. |
| 2017/0128226 A1 | 5/2017 | Faulhaber |
| 2017/0209284 A1 | 7/2017 | Overes et al. |
| 2017/0290674 A1 | 10/2017 | Olmos et al. |
| 2017/0290675 A1 | 10/2017 | Olmos et al. |
| 2017/0290677 A1 | 10/2017 | Olmos et al. |
| 2017/0296352 A1 | 10/2017 | Richerme et al. |
| 2018/0028200 A1 | 2/2018 | O'Neil et al. |
| 2018/0036141 A1 | 2/2018 | Oneil et al. |
| 2018/0256360 A1 | 9/2018 | Cain |
| 2018/0256362 A1 | 9/2018 | Slivka et al. |
| 2019/0083276 A1 | 3/2019 | Dimauro |
| 2019/0105171 A1 | 4/2019 | Rogers et al. |
| 2019/0133785 A1 | 5/2019 | Georges |
| 2019/0142602 A1 | 5/2019 | Olmos et al. |
| 2019/0269522 A1 | 9/2019 | Pavento et al. |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0078192 A1 | 3/2020 | Marchek et al. |
| 2020/0121473 A1 | 4/2020 | Gamache et al. |
| 2020/0129308 A1 | 4/2020 | Suedkamp et al. |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2020/0405500 A1 | 12/2020 | Cain |
| 2021/0000160 A1 | 1/2021 | Olmos et al. |
| 2021/0177619 A1 | 6/2021 | Voellmicke et al. |
| 2021/0353427 A1 | 11/2021 | Butler et al. |

FOREIGN PATENT DOCUMENTS

| | | |
|---|---|---|
| CA | 2617872 A1 | 2/2007 |
| CN | 1177918 | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| DE | 2804936 | 8/1979 |
| DE | 3023353 | 4/1981 |
| DE | 3801459 A1 | 8/1989 |
| DE | 3911610 | 10/1990 |
| DE | 9407806 U1 | 7/1994 |
| DE | 4012622 | 7/1997 |
| DE | 19710392 C1 | 7/1999 |
| DE | 19832798 | 11/1999 |
| DE | 20101793 | 5/2001 |
| DE | 202006005868 U1 | 6/2006 |
| DE | 202008001079 | 3/2008 |
| DE | 10357960 B4 | 9/2015 |
| EP | 077159 | 4/1983 |
| EP | 0260044 | 3/1988 |
| EP | 282161 | 9/1988 |
| EP | 0433717 | 6/1991 |
| EP | 0509084 A1 | 10/1992 |
| EP | 0525352 | 2/1993 |
| EP | 0529275 A2 | 3/1993 |
| EP | 0609084 A2 | 8/1994 |
| EP | 0611557 | 8/1994 |
| EP | 0621020 A1 | 10/1994 |
| EP | 0625336 | 11/1994 |
| EP | 678489 | 10/1995 |
| EP | 0743045 A2 | 11/1996 |
| EP | 0270704 | 6/1998 |
| EP | 1046376 | 4/2000 |
| EP | 1157676 A1 | 11/2001 |
| EP | 0853929 | 9/2002 |
| EP | 1283026 A2 | 2/2003 |
| EP | 1290985 | 3/2003 |
| EP | 1308132 A2 | 5/2003 |
| EP | 1378205 | 7/2003 |
| EP | 1374784 | 1/2004 |
| EP | 1405602 A1 | 4/2004 |
| EP | 1532949 | 5/2005 |
| EP | 1541096 | 6/2005 |
| EP | 1605836 A1 | 12/2005 |
| EP | 1385449 B1 | 7/2006 |
| EP | 1683593 | 7/2006 |
| EP | 1698305 B1 | 8/2007 |
| EP | 1829486 A1 | 9/2007 |
| EP | 1924227 A2 | 5/2008 |
| EP | 1925272 | 5/2008 |
| EP | 1843723 | 3/2010 |
| EP | 2368529 | 9/2011 |
| EP | 2237748 B1 | 9/2012 |
| EP | 1845874 | 10/2012 |
| EP | 2641571 A1 | 9/2013 |
| EP | 2705809 A1 | 3/2014 |
| EP | 2764851 | 8/2014 |
| EP | 2777633 | 9/2014 |
| EP | 2645965 B1 | 8/2016 |
| FR | 2649311 | 1/1991 |
| FR | 2699065 | 12/1992 |
| FR | 2728778 | 12/1994 |
| FR | 2712486 A1 | 5/1995 |
| FR | 2718635 | 10/1995 |
| FR | 2745709 | 3/1996 |
| FR | 2730159 | 8/1996 |
| FR | 2800601 | 11/1999 |
| FR | 2801189 | 11/1999 |
| FR | 2808182 | 4/2000 |
| FR | 2874814 | 3/2006 |
| FR | 2913331 A1 | 9/2008 |
| FR | 2948277 | 1/2011 |
| FR | 3026294 | 4/2016 |
| GB | 2157788 | 10/1985 |
| GB | 2173565 | 10/1986 |

(56) References Cited

FOREIGN PATENT DOCUMENTS

| | | |
|---|---|---|
| JP | 06-500039 | 6/1994 |
| JP | 06-319742 | 11/1994 |
| JP | 07-502419 | 3/1995 |
| JP | 07-184922 | 7/1995 |
| JP | 07-213533 A | 8/1995 |
| JP | 10-85232 | 4/1998 |
| JP | 11-89854 | 4/1999 |
| JP | 2003-010197 | 1/2003 |
| JP | 2003-126266 | 5/2003 |
| JP | 2003-526457 | 9/2003 |
| JP | 2006-501901 A | 1/2006 |
| JP | 2006-516456 | 7/2006 |
| JP | 2007-54666 | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 | 7/2011 |
| JP | 4988203 | 7/2011 |
| JP | 2012-020153 A | 2/2012 |
| JP | 2012-508048 A | 4/2012 |
| JP | 5164571 | 8/2012 |
| JP | 64-52439 | 12/2012 |
| JP | 2013-508031 | 3/2013 |
| JP | 2013-516206 A | 5/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| WO | WO 91/09572 | 12/1989 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | WO 93/04652 | 3/1993 |
| WO | 93/17669 A1 | 9/1993 |
| WO | WO 1994/004100 | 3/1994 |
| WO | WO 1995/031158 | 11/1995 |
| WO | WO 96/28100 | 9/1996 |
| WO | WO 97/00054 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | WO 99/42062 | 8/1999 |
| WO | WO 99/52478 | 10/1999 |
| WO | WO 1999/053871 | 10/1999 |
| WO | 99/60956 A1 | 12/1999 |
| WO | 99/63914 A1 | 12/1999 |
| WO | WO 99/62417 | 12/1999 |
| WO | 00/13620 A1 | 3/2000 |
| WO | WO 2000/012033 | 3/2000 |
| WO | 00/24343 A1 | 5/2000 |
| WO | WO 00/67652 | 5/2000 |
| WO | 00/44288 A1 | 8/2000 |
| WO | 00/67650 A1 | 11/2000 |
| WO | 00/67651 A1 | 11/2000 |
| WO | WO 00/74605 | 12/2000 |
| WO | WO 00/76409 | 12/2000 |
| WO | WO 00/53127 | 1/2001 |
| WO | WO 01/01895 | 1/2001 |
| WO | WO 2001/001893 | 1/2001 |
| WO | 01/10316 A1 | 2/2001 |
| WO | WO 01/12054 | 2/2001 |
| WO | WO 2001/017464 | 3/2001 |
| WO | 01/68004 A2 | 9/2001 |
| WO | WO 01/80751 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43628 A1 | 6/2002 |
| WO | 02/45627 A1 | 6/2002 |
| WO | 02/47563 A1 | 6/2002 |
| WO | WO 02/43601 | 6/2002 |
| WO | 02/71921 A2 | 9/2002 |
| WO | 02/85250 A2 | 10/2002 |
| WO | 03/02021 A2 | 1/2003 |
| WO | 03/05937 A1 | 1/2003 |
| WO | 03/07854 A1 | 1/2003 |
| WO | 03/20169 A2 | 3/2003 |
| WO | 03/22165 A1 | 3/2003 |
| WO | WO 03/21308 | 3/2003 |
| WO | 03/28587 A2 | 4/2003 |
| WO | WO 03/43488 | 5/2003 |
| WO | 03/03951 A1 | 6/2003 |
| WO | 2003/101308 A1 | 12/2003 |
| WO | WO 2004/008949 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/069033 A2 | 8/2004 |
| WO | WO 2004/064603 | 8/2004 |
| WO | 2004/073563 A2 | 9/2004 |
| WO | 2004/080316 A1 | 9/2004 |
| WO | 2004/082526 A2 | 9/2004 |
| WO | WO 2004/078220 | 9/2004 |
| WO | WO 2004/078221 | 9/2004 |
| WO | 2004/098420 A2 | 11/2004 |
| WO | WO 2004/098453 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/115261 A1 | 12/2005 |
| WO | WO 2005/112834 | 12/2005 |
| WO | WO 2005/112835 | 12/2005 |
| WO | WO 2006/017507 | 2/2006 |
| WO | 2006/044920 A2 | 4/2006 |
| WO | 2006/047645 A2 | 5/2006 |
| WO | WO 2006/047587 | 5/2006 |
| WO | 2006/058079 A2 | 6/2006 |
| WO | 2006/060420 A1 | 6/2006 |
| WO | 2006/066228 A2 | 6/2006 |
| WO | WO 2006/058281 | 6/2006 |
| WO | WO 2006/063083 | 6/2006 |
| WO | WO 2006/065419 | 6/2006 |
| WO | 2006/072941 A2 | 7/2006 |
| WO | WO 2006/081843 | 8/2006 |
| WO | WO 2006/108067 | 10/2006 |
| WO | 2006/118944 A1 | 11/2006 |
| WO | WO 2007/009107 | 1/2007 |
| WO | 2007/022194 A2 | 2/2007 |
| WO | WO 2007/028098 | 3/2007 |
| WO | WO 2007/048012 | 4/2007 |
| WO | 2007/067726 A2 | 6/2007 |
| WO | 2007/084427 A2 | 7/2007 |
| WO | WO 2007/119212 | 10/2007 |
| WO | 2008/005627 A2 | 1/2008 |
| WO | 2008/011378 A1 | 1/2008 |
| WO | WO 2007/124130 | 4/2008 |
| WO | WO 2008/044057 | 4/2008 |
| WO | WO 2008/064842 | 6/2008 |
| WO | WO 2008/070863 | 6/2008 |
| WO | 2008/103781 A2 | 8/2008 |
| WO | 2008/103832 A1 | 8/2008 |
| WO | WO 2009/064787 | 5/2009 |
| WO | WO 2009/092102 | 7/2009 |
| WO | WO 2009/124269 | 10/2009 |
| WO | WO 2009/143496 | 11/2009 |
| WO | WO 2009/147527 | 12/2009 |
| WO | WO 2009/152919 | 12/2009 |
| WO | 2010/011348 A1 | 1/2010 |
| WO | WO 2010/068725 | 6/2010 |
| WO | 2010/075451 A1 | 7/2010 |
| WO | 2010/075555 A2 | 7/2010 |
| WO | 2010/088766 A1 | 8/2010 |
| WO | 2010/121002 A1 | 10/2010 |

(56) References Cited

FOREIGN PATENT DOCUMENTS

| | | |
|---|---|---|
| WO | WO 2010/136170 | 12/2010 |
| WO | WO 2010/148112 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | WO 2011/079910 | 7/2011 |
| WO | 2011/119617 A1 | 9/2011 |
| WO | WO 2011/142761 | 11/2011 |
| WO | WO 2011/150350 | 12/2011 |
| WO | WO 2012/009152 | 1/2012 |
| WO | 2012/027490 A2 | 3/2012 |
| WO | 2012/028182 A1 | 3/2012 |
| WO | 2012/030331 A1 | 3/2012 |
| WO | 2012/047712 | 4/2012 |
| WO | WO 2012/089317 | 7/2012 |
| WO | 2012/103254 A2 | 8/2012 |
| WO | 2012/122294 A1 | 9/2012 |
| WO | 2012/129197 A1 | 9/2012 |
| WO | WO 2012/135764 | 10/2012 |
| WO | WO 2013/006669 | 1/2013 |
| WO | WO 2013/023096 | 2/2013 |
| WO | WO 2013/025876 | 2/2013 |
| WO | WO 2013/043850 | 5/2013 |
| WO | WO 2013/062903 | 5/2013 |
| WO | WO 2013/082184 | 6/2013 |
| WO | 2013/148176 A1 | 10/2013 |
| WO | 2013/149611 A1 | 10/2013 |
| WO | WO 2013/158294 | 10/2013 |
| WO | WO 2013/173767 | 11/2013 |
| WO | WO 2013/184946 | 12/2013 |
| WO | 2014/014610 A1 | 1/2014 |
| WO | WO 2014/018098 | 1/2014 |
| WO | WO 2014/026007 | 2/2014 |
| WO | WO 2014/035962 | 3/2014 |
| WO | WO 2014/088521 | 6/2014 |
| WO | WO 2014/116891 | 7/2014 |
| WO | WO 2014/144696 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | WO 2016/069796 | 5/2016 |
| WO | 2016/118246 A1 | 7/2016 |
| WO | WO 2016/127139 | 8/2016 |
| WO | 2017/136620 A1 | 8/2017 |

OTHER PUBLICATIONS

U.S. Appl. No. 14/685,358, filed Apr. 13, 2015, Marden et al.
U.S. Appl. No. 14/685,402, filed Apr. 13, 2015, Cain.
U.S. Appl. No. 14/790,866, filed Jul. 2, 2015, Thommen et al.
U.S. Appl. No. 61/675,975, filed Jul. 26, 2012, Lechmann et al.
Alfen et al., "Developments in the Area of Endoscopic Spine Surgery", European Musculoskeletal Review 2006, pp. 23-24. ThessysTM, Transforminal Endoscopic Spine Systems. Medical Solutions ioimax.
Brochure for PERPOS PLS System Surgical Technique by Interventional Spine, 2008.
Paul D. Fuchs, "The use of an interspinous implant in conjunction with a graded facetectomy procedure", Spine vol. 30, No. 11, pp. 1266-1272, 2005.
Iprenburg et al., "Transforaminal Endoscopic Surgery in Lumbar Disc Herniation in an Economic Crisis—The TESSYS Method", US Musculoskeletal, 2008, pp. 47-49.
King, M.D., Don, "Internal Fixation for Lumbosacral Fusion", "The Journal of Bone and Joint Surgery", J. Bone Joint Surg Am., 1948; 30: 560-578.
Morgenstern R; "Transforaminal Endoscopic Stenosis Surgery—A Comparative Study of Laser and Reamed Foraminoplasty", in European Musculoskeletal Review, Issue 1, 2009.
ProMap TM EMG Navigation Probe. Technical Brochure Spineology Inc., Dated May 2009.
Chin, Kingsley R., M.D. "Early Results of the Triage Medical Percutaneous Transfacet Pedicular BONE-LOK Compression Device for Lumbar Fusion", accessed online Jul. 10, 2017, 10 pages.
Niosi, Christina A., "Biomechanical Characterization of the three-dimentinoal kinematic behavior of the Dynesys dynamic stabilization system: an in vitro study", Eur Spine J. (2006) 15: pp. 913-922.
Manal Siddiqui, "The Positional Magnetic Resonance Imaging Changes in the Lumbar Spine Following Insertion of a Novel Interspinous Process Distraction Device", Spine vol. 30, No. 23, pp. 2677-2682, 2005.
Vikram Talwar, " Insertion loads of the X Stop Interspinous Process Distraction System Designed to Treat Neurogenic Intermittent Claudication", Eur Spine J. (2006) 15: pp. 908-912.
James F. Zucherman, "A Multicenter, Prospective, Randomized Trial Evaluating the X Stop Interspinous Process Decompression System for the Treatment of Neurogenic Intermittent Claudication", Spine, vol. 30, No. 12, pp. 1351-1358, 2005.
Kambin et al., "Percutaneous Lateral Discectomy of the Lumbar Spine: A Preliminary Report"; Clin. Orthop.; 1993; 174: 127-132.
Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Brooks, M.D. et al., Efficacy of Supplemental Posterior Transfacet Pedicle Device Fixation in the Setting of One- or Two-Level Anterior Lumbar Interbody Fusion, retrieved Jun. 19, 2017, 6 pages.
International Patent Application No. PCT/US2013/029014, International Search Report dated Jul. 1, 2013, 7 pages.
Chiang, Biomechanical Comparison of Instrumented Posterior Lumbar Interbody Fusion with One or Two Cages by Finite Element Analysis, Spine, 2006, pp. E682-E689, vol. 31(19), Lippincott Williams & Wilkins, Inc.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hunt, Expanable cage placement via a posterolateral approach in lumbar spine reconstructions, Journal of Neurosurgery: Spine, 2006, pp. 271-274, vol. 5.
Krbec, [Replacement of the vertebral body with an expansion implant (Synex)], Acta Chir Orthop Traumatol Cech, 2002, pp. 158-162, vol. 69(3).
Polikeit, The importance of the endplate for interbody cages in the lumbar spine, Eur Spine J, 2003, pp. 556-561, vol. 12.
Shin, Posterior Lumbar Interbody Fusion via a Unilateral Approach, Yonsei Medical Journal, 2006, pp. 319-325, vol. 47(3).
Hoogland, T. et al., Total Lumbar Intervertebral Disc Replacement: testing of a New Articulating Space in Human Cadaver Spines—24 1 Annual ORS, Dallas TX, Feb. 21-23, 1978, 8 pages.
European Search Report EP03253921 dated Nov. 13, 2003, 4 pages.
*Spine Solutions Brochure—Prodisc 2001*, 16 pages.
Link SB Charite Brochure—Intervertebral Prosthesis 1988, 29 pages.
Grays Anatomy, Crown Publishers, Inc., 1977, pp. 33-54.
Method and Apparatus for Spinal Fixation, U.S. Appl. No. 60/794,171, filed Apr. 21, 2006.
U.S. Appl. No. 60/942,998, Method and Apparatus for Spinal Stabilization, filed Jun. 8, 2007.
U.S. Appl. No. 60/397,588, Method and apparatus for spinal fixation, filed Jul. 19, 2002.
U.S. Appl. No. 60/424,055, filed Nov. 5, 2002, entitled Method and apparatus for spinal fixation.
[No Author Listed] Porocoat® Porous Coating, Depuy Synthes Companies, 2015, 2 pages, webpage, accessed Jul. 5, 2016, <https://emea.depuysynthes.com/hcp/hip/products/qs/porocoat-porous-coating-emea>.

(56) References Cited

OTHER PUBLICATIONS

Bolder et al., Monoclonal antibodies reactive with human osteogenic cell surface antigens. Bone. Sep. 1997; 21 (3):225-235.

Bruder et al., Identification and characterization of a cell surface differentiation antigen on human osteoprogenitor cells. 42nd Annual Meeting of the Orthopaedic Research Society, p. 574, Feb. 19-22, 1996, Atlanta, Georgia.

Burkoth et al., A review of photocrosslinked polyanhydrides: in situ forming degradable networks. Biomaterials. Dec. 2000; 21 (23): 2395-2404.

Cambridge Scientific News, FDA Approves Cambridge Scientific, Inc.'s Orthopedic Wisorb (TM) Malleolar Screw [online], Jul. 30, 2002 [retrieved on Oct. 14, 2003]. Retrieved from the Internet <URL: http://www.cambridgescientificinc.com>.

Carrino, John A., Roxanne Chan and Alexander R. Vaccaro, "Vertebral Augmentation: Vertebroplasty and Kyphoplasty", Seminars in Roentgenology, vol. 39, No. 1 (Jan.), 2004: pp. 68-84.

Cheng, B.C., Ph.D., Biomechanical pullout strength and histology of Plasmapore® XP coated implants: Ovine multi time point survival study. Aesculap Implant Systems, LLC, 2013, 12 pages.

CN Office Action dated Apr. 24, 2020 for CN Application No. 201780040910.

Edeland, H.G., "Some Additional Suggestions For An Intervertebral Disc Prosthesis", J of Bio Medical Engr., vol. 7(1) pp. 57-62, Jan. 1985.

Flemming et al., Monoclonal anitbody against adult marrow-derived mesenchymal stem cells recognizes developing vasculature in embryonic human skin. Developmental Dynamics 1998; 212:119-132.

Ha, S. W. et al., Topographical characterization and microstructural interface analysis of vacuum-plasma-sprayed titanium and hydroxyapatite coatings on carbon fibre-reinforced poly(etheretherketone), J. Mater. Sci.: Materials in Medicine, 1997, v. 8, pp. 891-896.

Haas, Norbert P., New Products from AO Development [online], May 2002 [retrieved on Oct. 14, 2003], Retrieved from the Internet <URL: http://www.ao.asif.ch/development/pdf_tk_news_02.pdf>.

Hao et al., Investigation of nanocomposites based on semi-interpenetrating network of [L—poly (epsilon-caprolactone)]/[net-poly (epsilon-caprolactone)] and hydroxyapatite nanocrystals. Biomaterials. Apr. 2003; 24(9): 1531-9.

Harsha et al., Tribo performance of polyaryletherketone composites, Polymer Testing (21) (2002) pp. 697-709.

Haynesworth et al., Cell surface antigens on human marrow-derived mesenchymal cells are detected by monoclonal antibodies. Bone. 1992; 13(1):69-80.

Hitchon et al., Comparison of the biomechanics of hydroxyapatite and polymethylmethacrylate vertebroplasty in a cadaveric spinal compression fracture model. J Neurosurg Oct. 2001;95(2 Suppl):215-20.

Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.

Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).

Kotsias, A., Clinical trial of titanium-coated PEEK cages anterior cervical discectomy and fusion. [Klinishe Untersuching zum Einsatz von titanbeschichteten Polyetheretherketon—Implantaten bei der cervikalen interkorporalen fusion]. Doctoral thesis. Department of Medicine, Charite, University of Medicine Berlin, 2014, 73 pages (German language document/Engl. summary).

Kroschwitz et al., eds., Hydrogels. Concise Encyclopedia of Polymer Science and Engineering. Wiley and Sons, pp. 458-459, 1990.

Lendlein et al., AB-polymer networks based on oligo(epsilon-caprolactone) segments showing shape-memory properties. Proc Natl Acad Sci US A. Jan. 30, 2001; 98(3):842-7. Epub Jan. 23, 2001.

Malberg. M.I., MD; Pimenta, L., MD; Millan, M.M., MD, 9th International Meeting on Advanced Spine Techniques, May 23-25, 2002, Montreux, Switzerland. Paper #54, Paper #60, and E-Poster#54, 5 pages.

McAfee et al., Minimally invasive anterior retroperitoneal approach to the lumbar spine: Emphasis on the lateral BAK. SPINE. 1998; 23(13): 1476-84.

Mendez et al., Self-curing acrylic formulations containing PMMA/PCL composites: properties and antibiotic release behavior. J Biomed Mater Res. Jul. 2002;61 (1 ):66-74.

Nguyen et al., Poly(Aryl-Ether-Ether-Ketone) and its Advanced Composites: A Review, Polymer Composites, Apr. 1987, vol. 8, No. 2, pp. 57-73.

Osteoset Registered DBM Pellets (Important Medical Information) [online], Nov. 2002 [retrieved on Oct. 14, 2003] Retrieved from the Internet <URL: http://www.wmt.com/Literature>.

Regan et al., Endoscopic thoracic fusion cage. Atlas of Endoscopic Spine Surgery. Quality Medical Publishing, Inc. 1995; 350-354.

Slivka et al., In vitro compression testing of fiber-reinforced, bioabsorbable, porous implants. Synthetic Bioabsorbable Polymers for Implants. STP1396, pp. 124-135, ATSM International, Jul. 2000.

Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/crdocs/cfPMA/pma.cfm?id-14736#>. 4 pages, 2012.

Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

Timmer et al., In vitro degradation of polymeric networks of poly(propylene fumarate) and the crosslinking macromer poly(propylene fumarate)-diacrylate. Biomaterials. Feb. 2003;24(4 ):571-7.

United States Disctrict Court, Central District of California, Case No. 1 :10-CV-00849-LPS, *Nuvasive, Inc.*, vs., *Globus Medical, Inc.*, Videotaped Deposition of: Luiz Pimenta, M.D., May 9, 2012, 20 pages.

U.S. Appl. No. 09/558,057, filed Apr. 26, 2000, entitled Bone Fixation System.

Walsh et al., Preparation of porous composite implant materials by in situ polymerization of porous apatite containing epsilon-caprolactone or methyl methacrylate Biomaterials. Jun. 2001; 22(11): 1205-12.

Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.

U.S. Appl. No. 55/458,27, dated Oct. 3, 1995, Aust.

Allcock, "Polyphosphazenes"; The Encyclopedia of Polymer Science; 1988; pp. 31-41; vol. 13; Wiley Intersciences, John Wiley & Sons.

Cohn, "Biodegradable PEO/PLA Block Copolymers"; Journal of Biomedical Materials Research; 1988; pp. 993-1009 vol. 22; John Wiley & Sons, Inc.

Cohn, "Polymer Preprints"; Journal of Biomaterials Research; 1989; p. 498; Biomaterials Research Labortatory, Casali Institute of Applied Chemistry, Israel.

Heller, "Poly (Otrho Esters)"; Handbook of Biodegradable Polymers; edited by Domb; et al; Hardwood Academic Press; 1997; pp. 99-118.

Japanese Office Action for Application No. 2013-542047, dated Sep. 8, 2015 (12 pages).

Japanese Office Action for Application No. 2016-135826, dated Jun. 6, 2017, (7 pages).

Kemnitzer, "Degradable Polymers Derived From the Amino Acid L-Tyrosine"; 1997; pp. 251-272; edited by Domb, et al., Hardwood Academic Press.

Khoo, "Minimally Invasive Correction of Grade I and II Isthmic Spondylolisthesis using AxiaLIF for L5/S1 Fusion", pp. 1-7, Rev B Sep. 15, 2008.

U.S. Appl. No. 61/009,546, filed Dec. 28, 2007 Rodgers.

U.S. Appl. No. 61/140,926, filed Dec. 26, 2008 Spann.

U.S. Appl. No. 61/178,315, filed May 14, 2009 Spann.

(56) References Cited

OTHER PUBLICATIONS

Vandorpe, "Biodegradable Polyphosphazenes for Biomedical Applications"; Handbook of Biodegradable Polymers; 1997; pp. 161-182; Hardwood Academic Press.

* cited by examiner

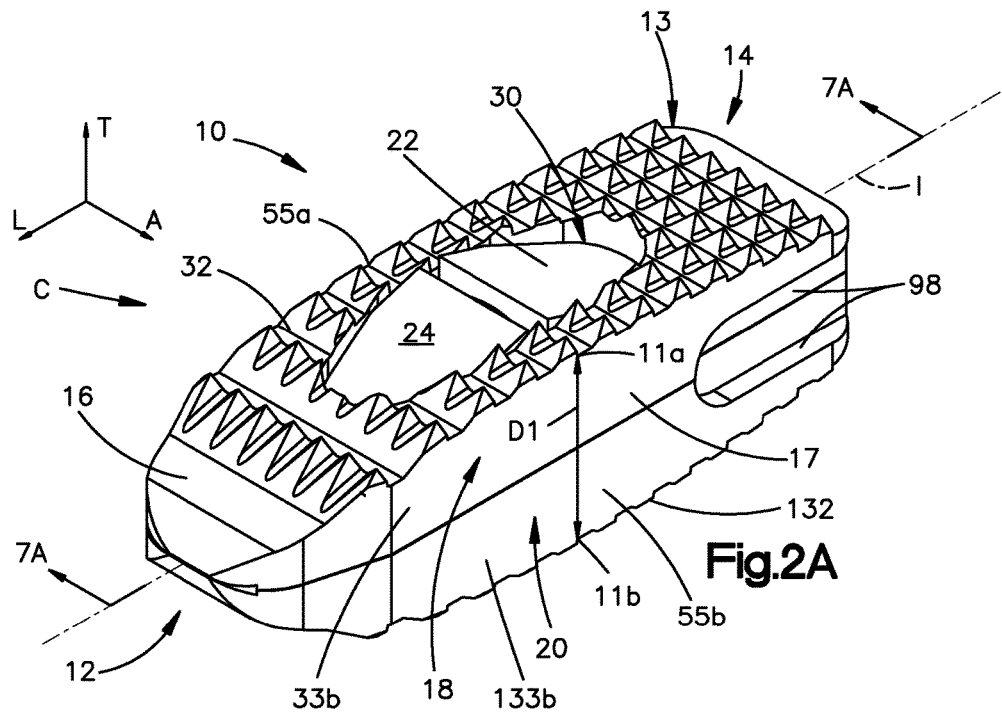
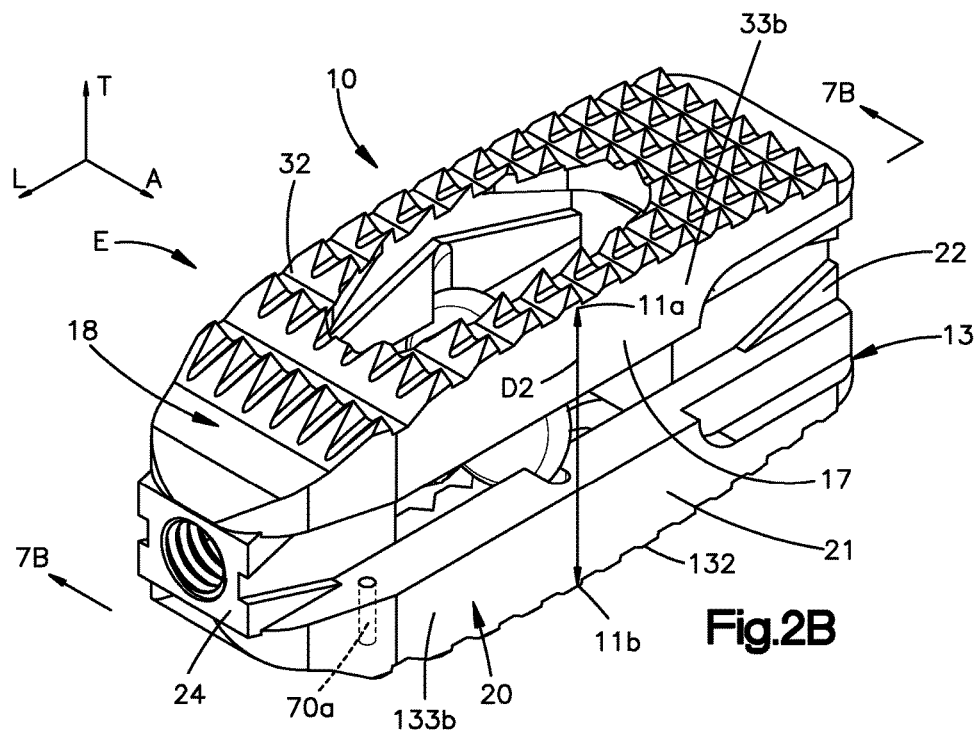

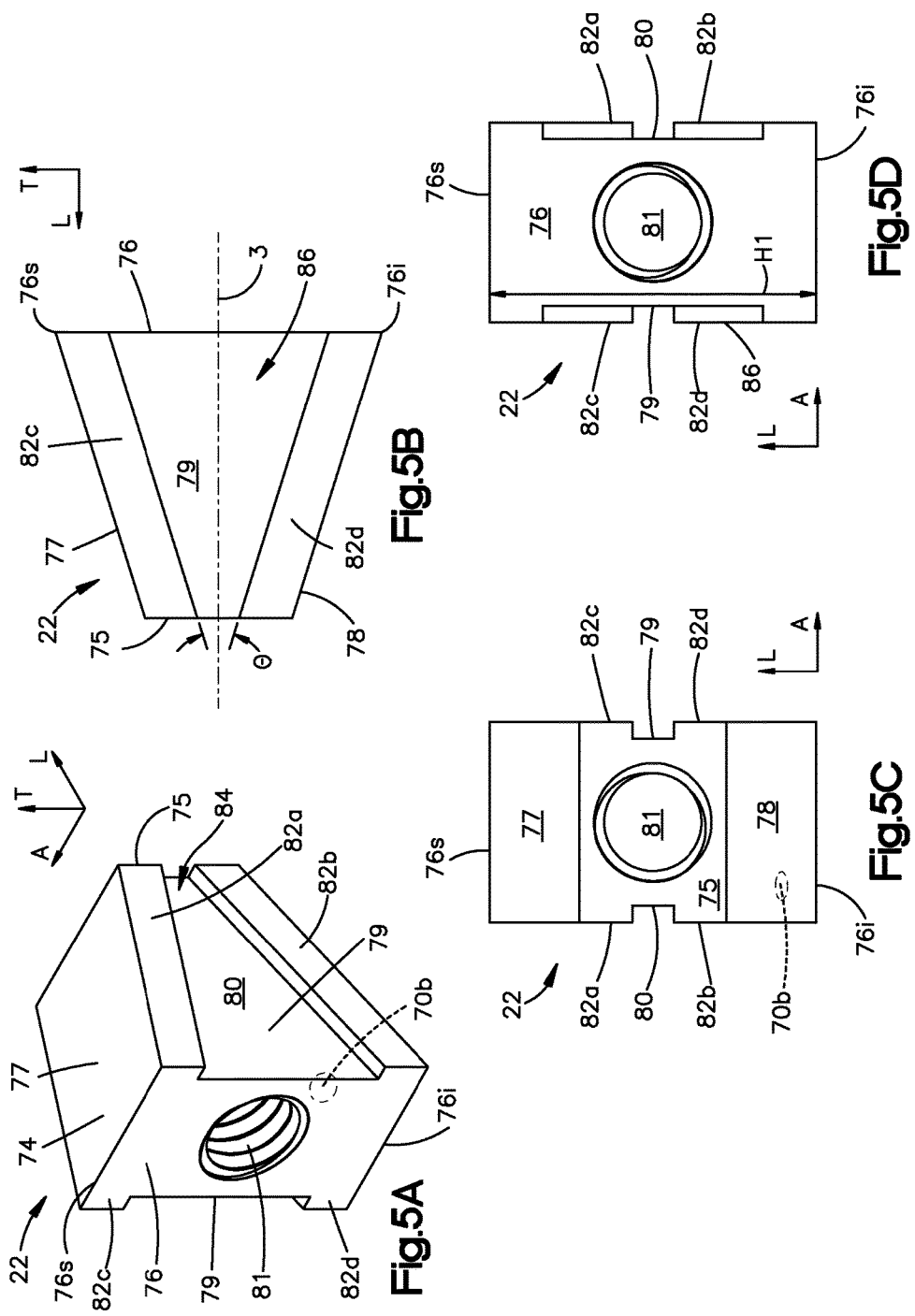

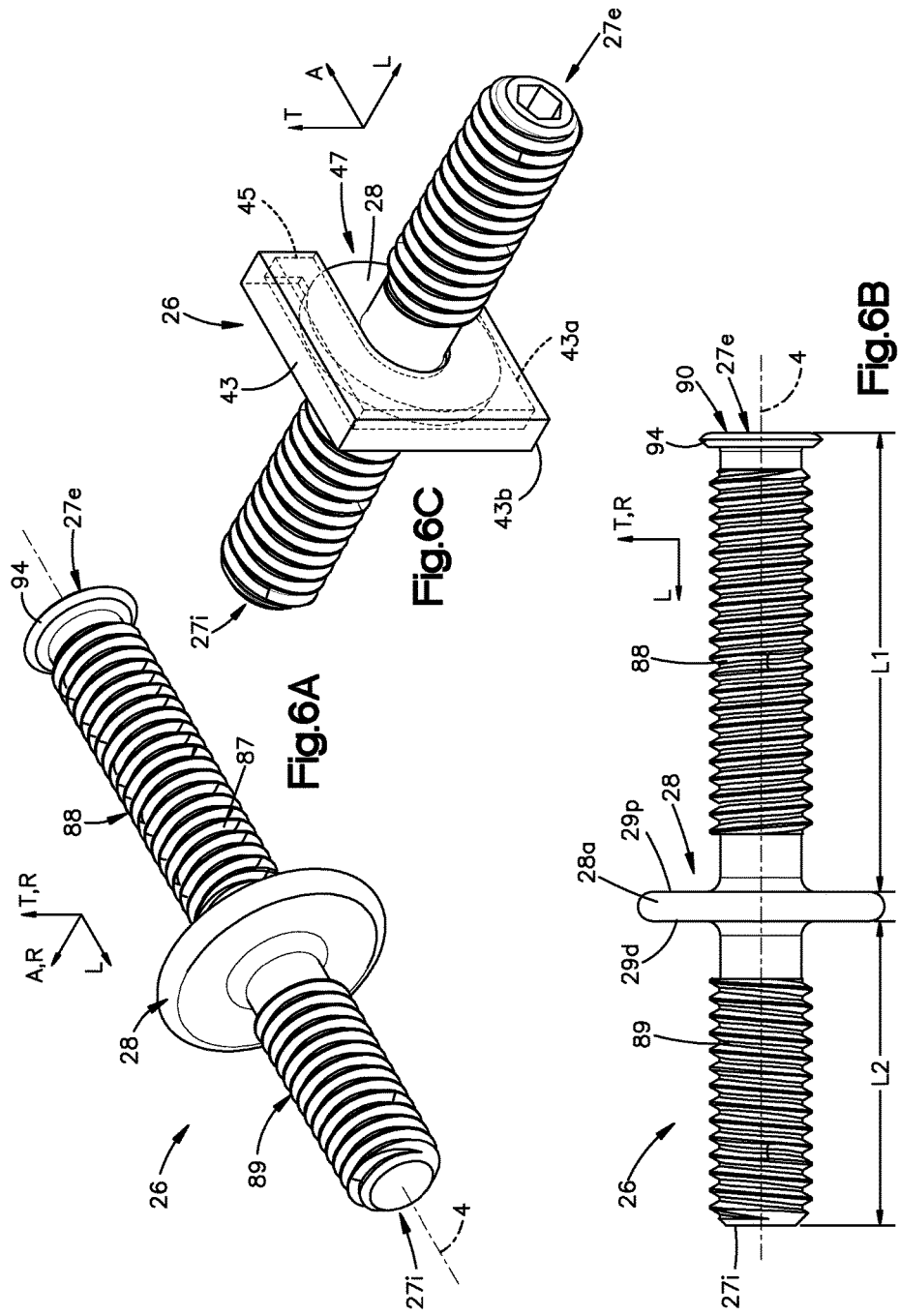

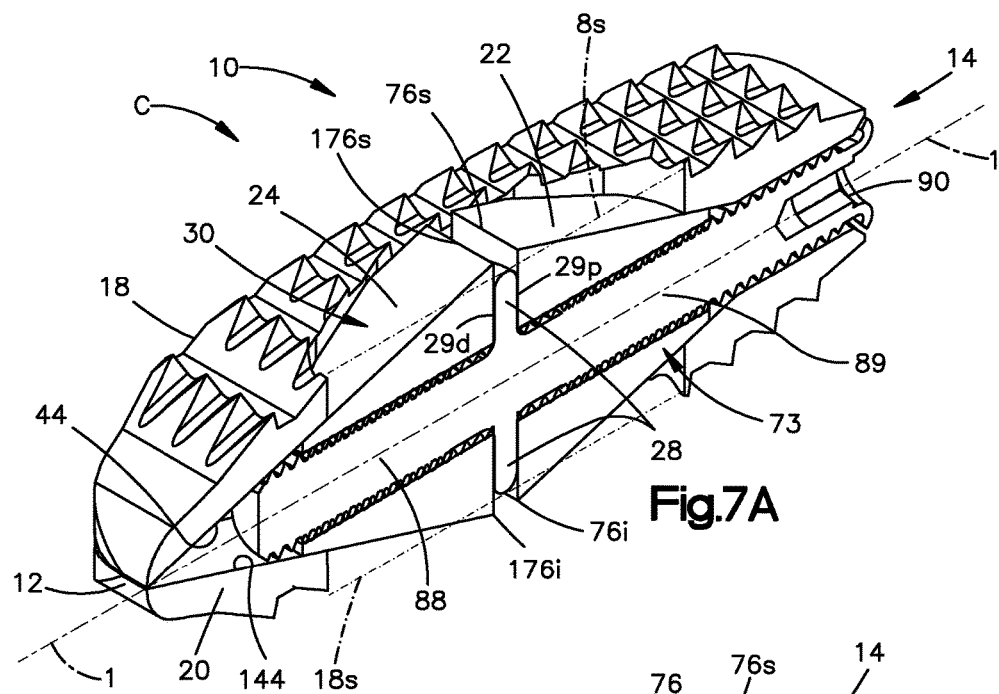
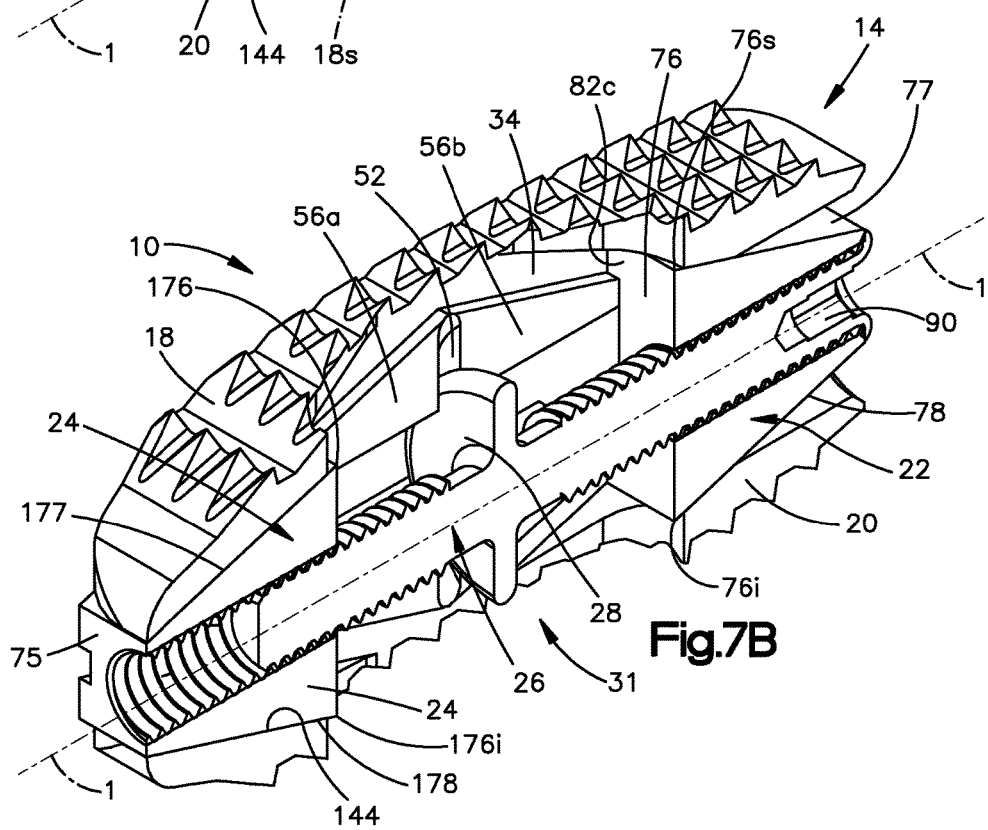

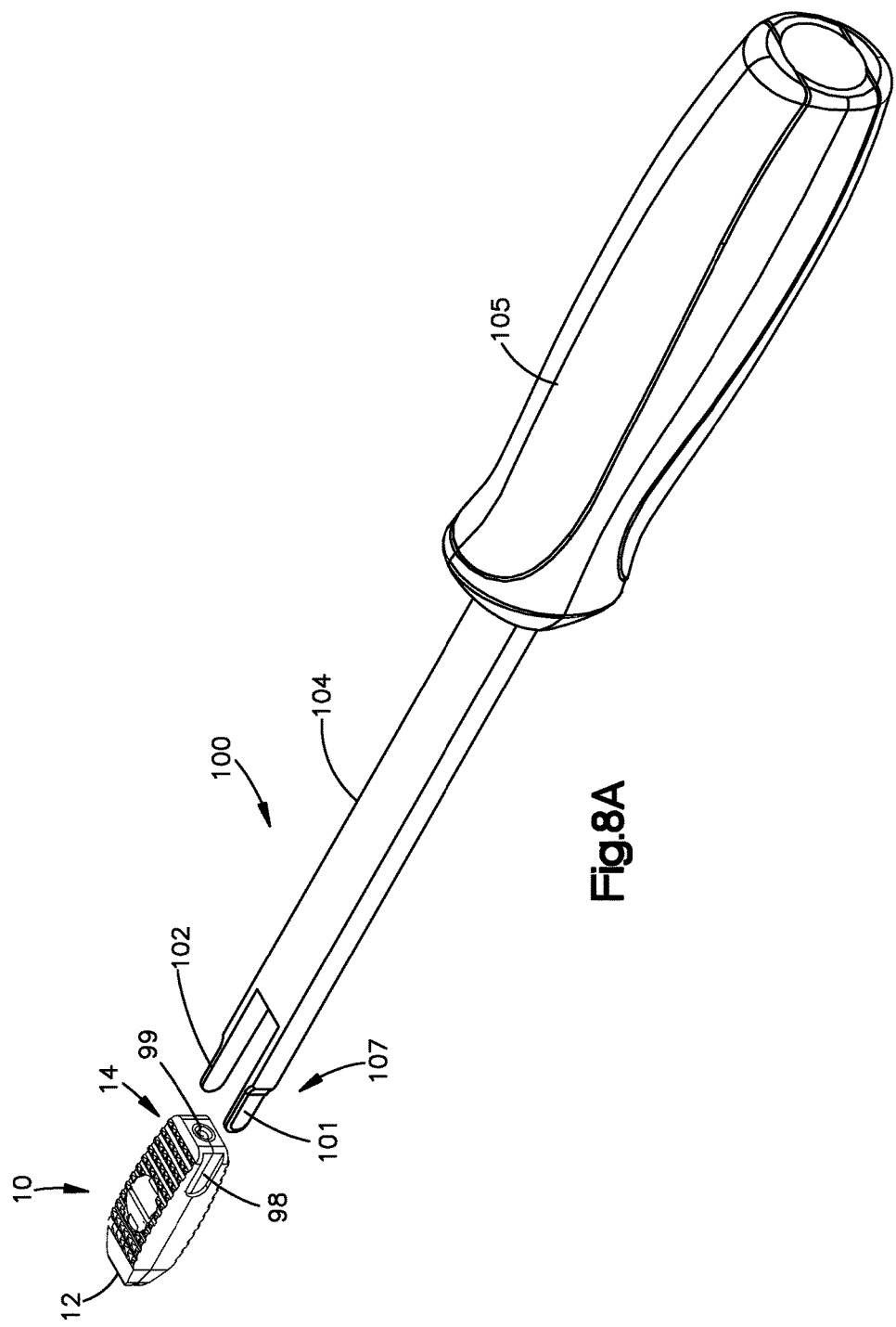

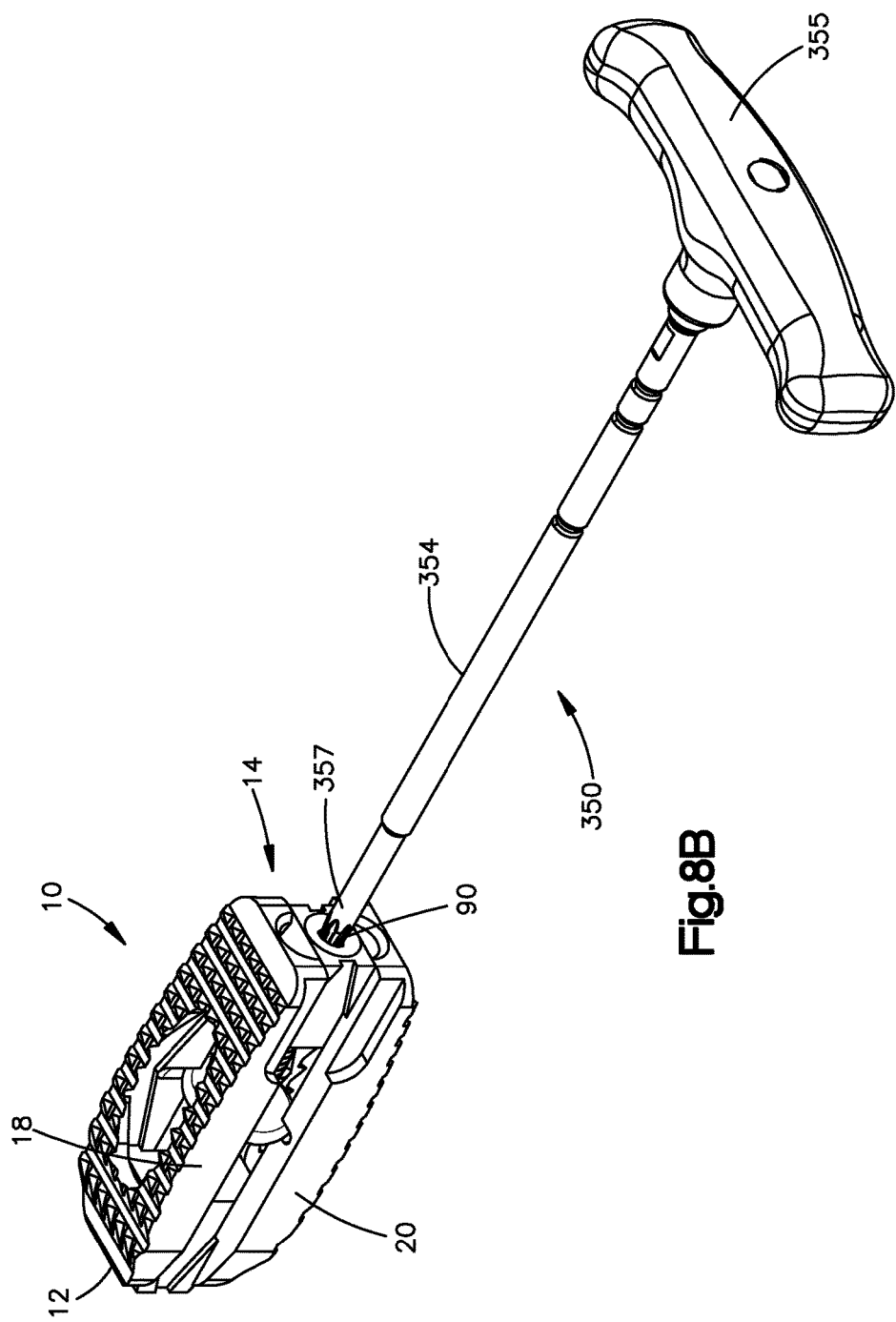

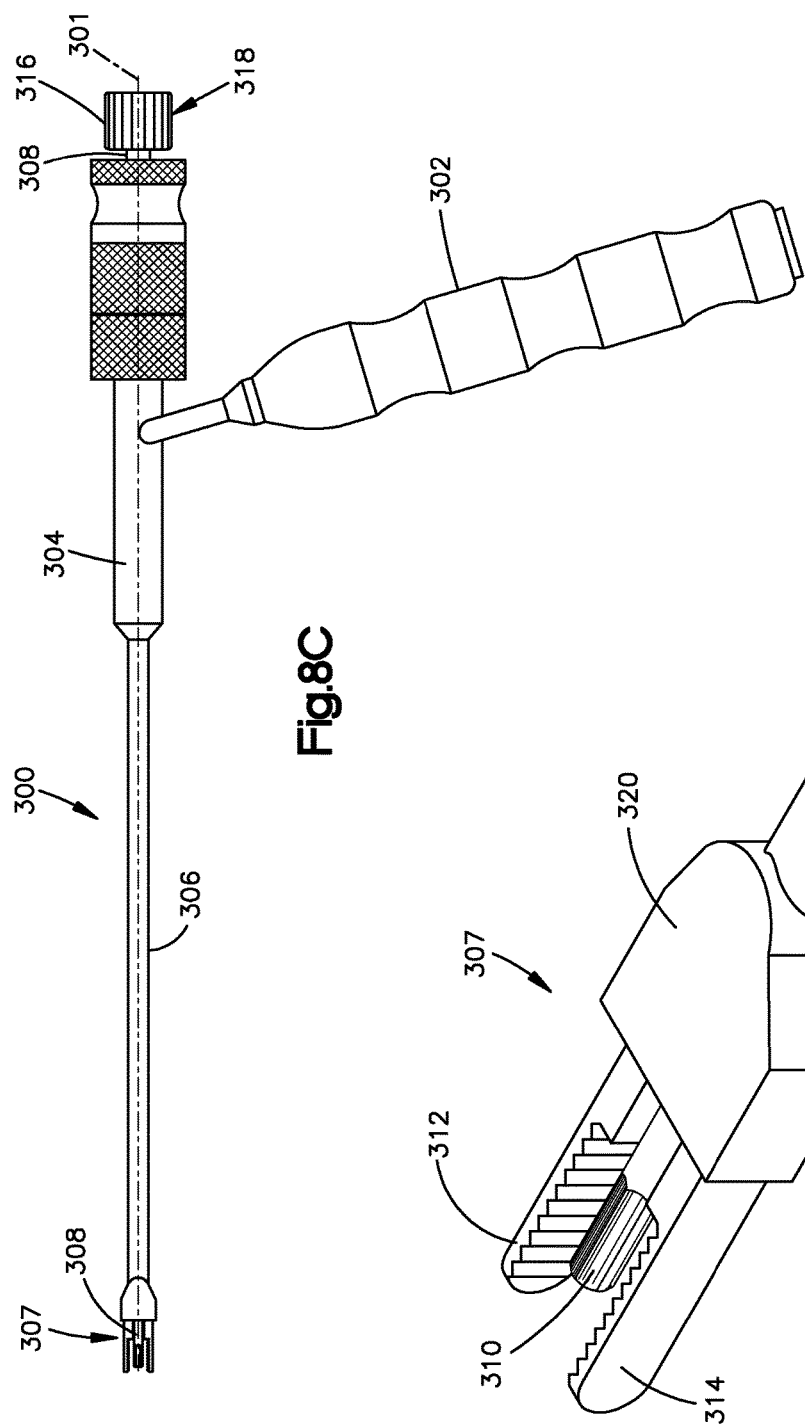

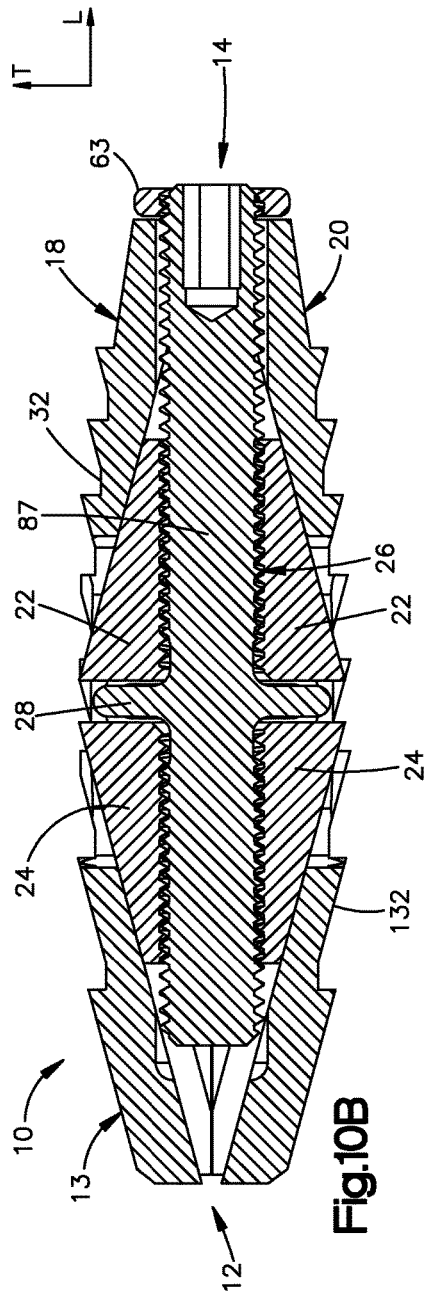
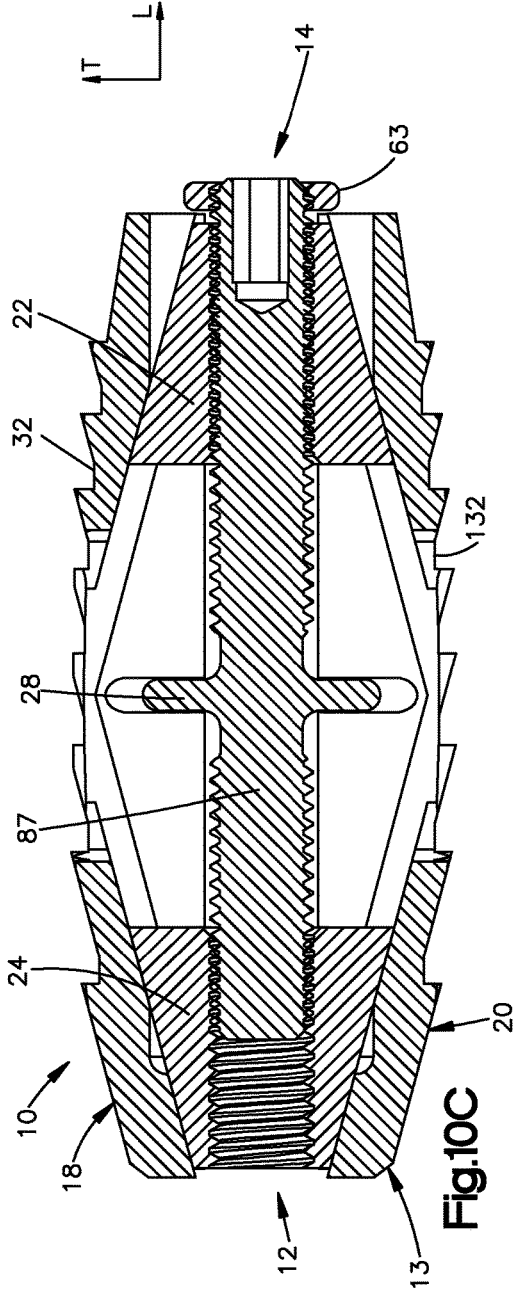
Fig.10B
Fig.10C

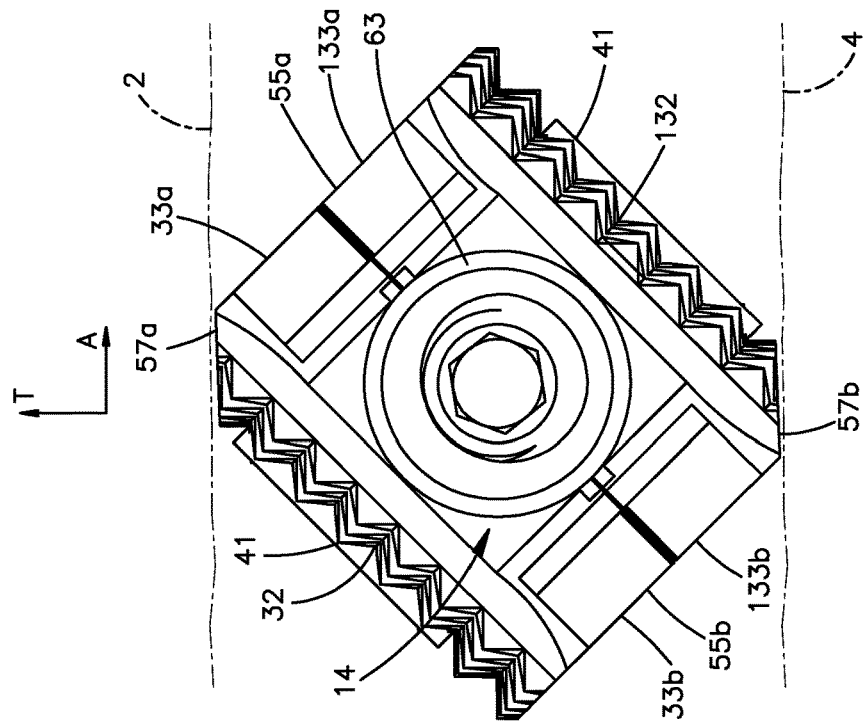
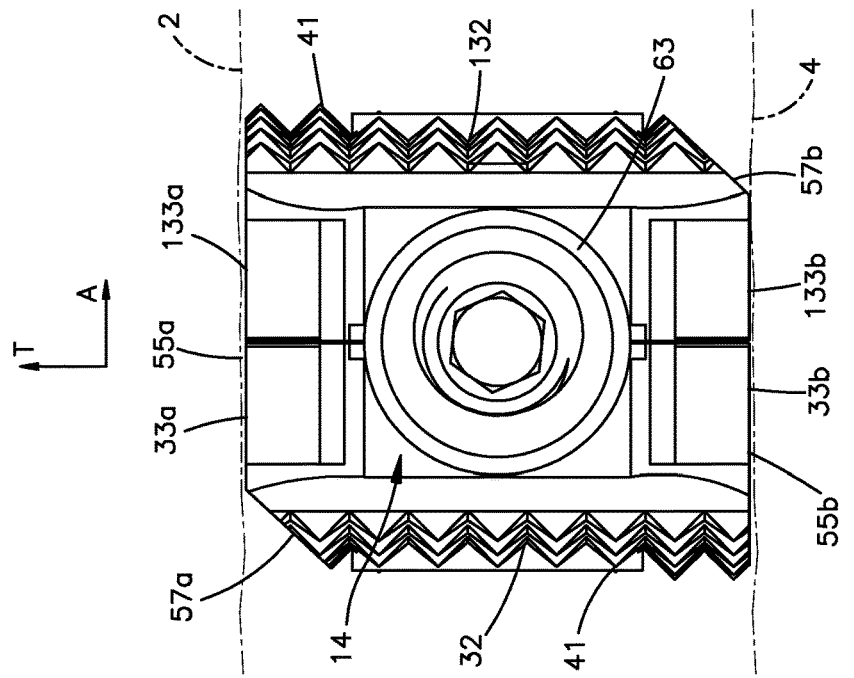

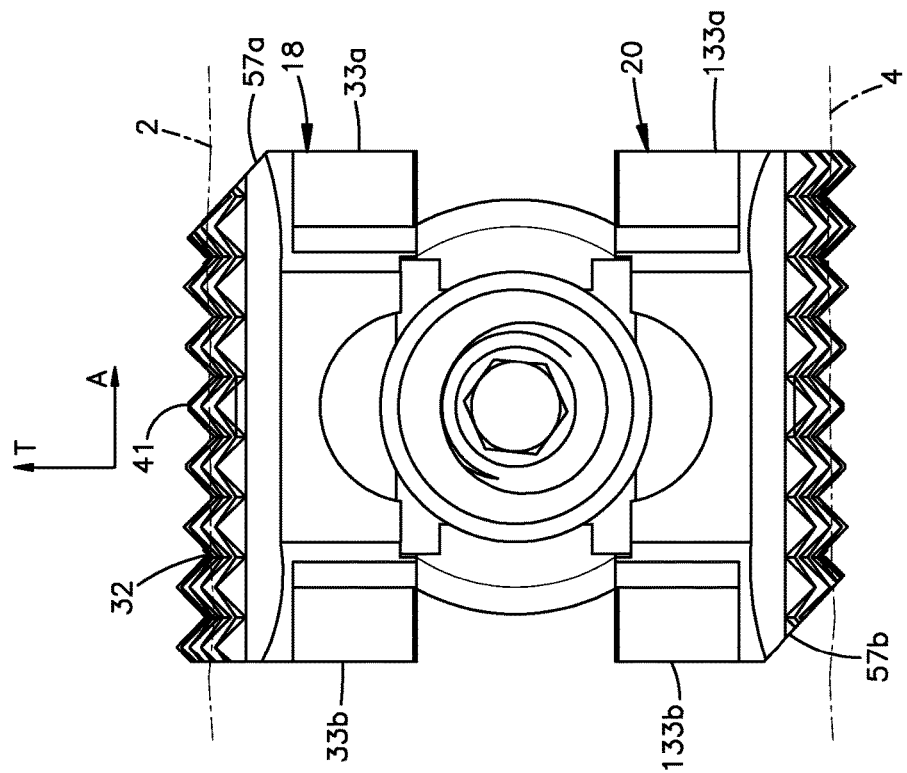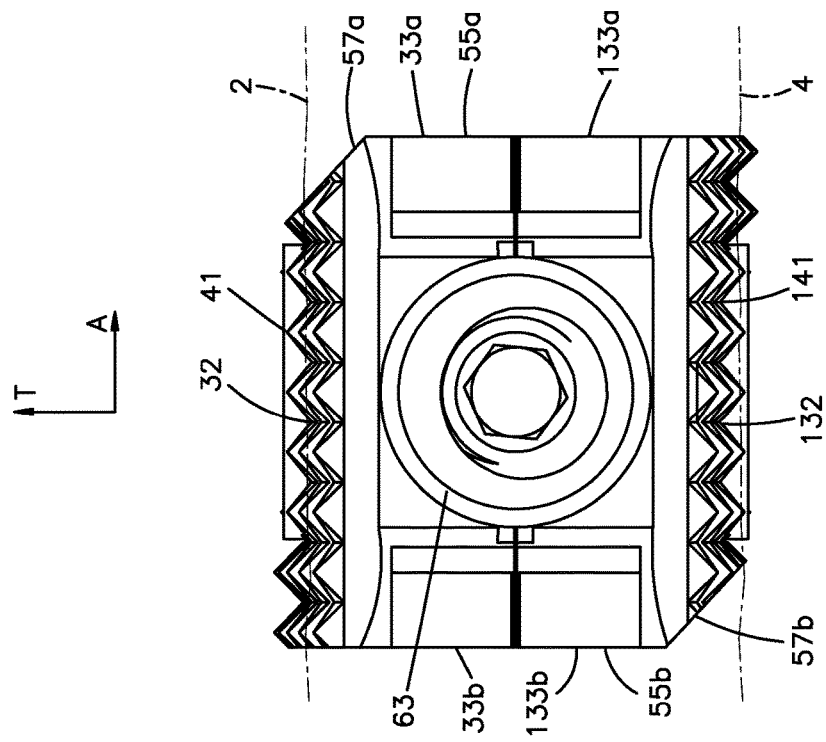

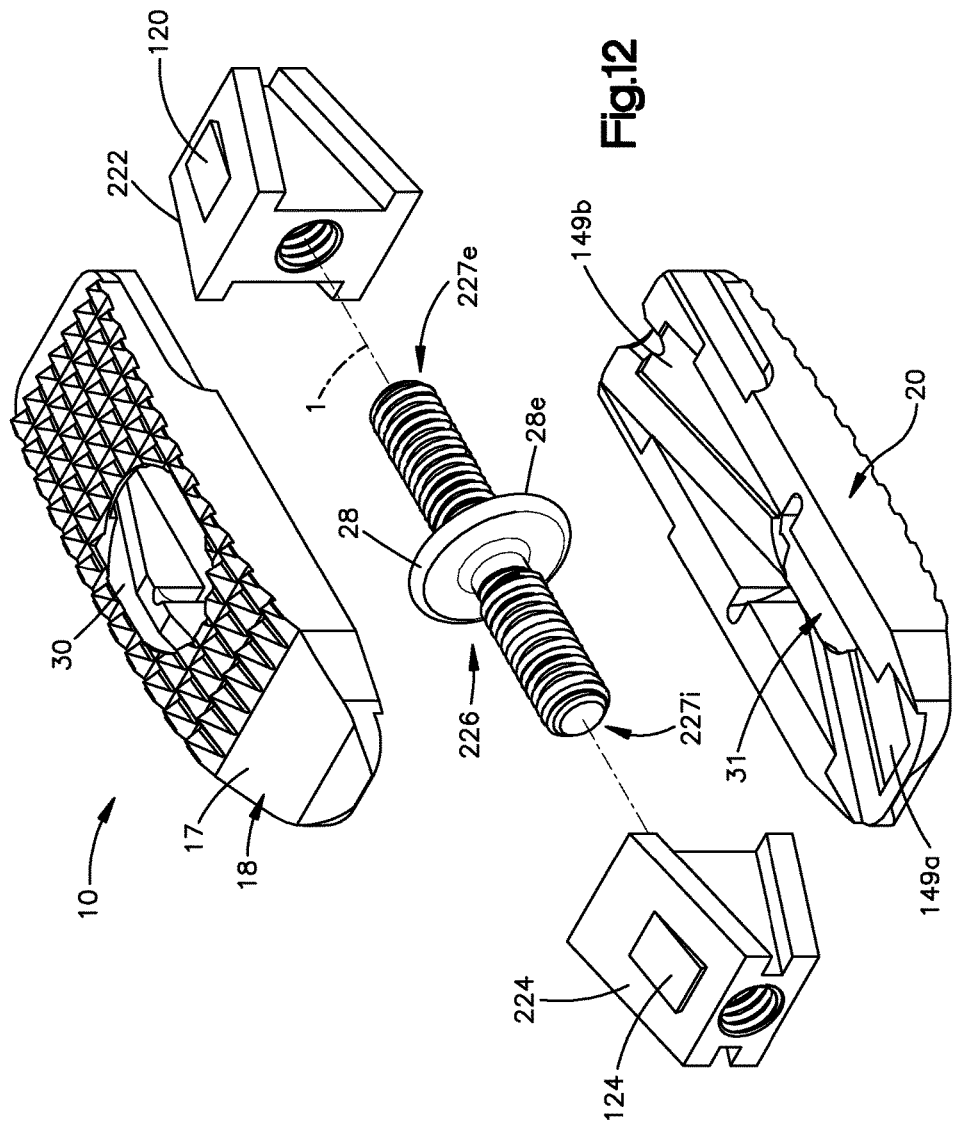

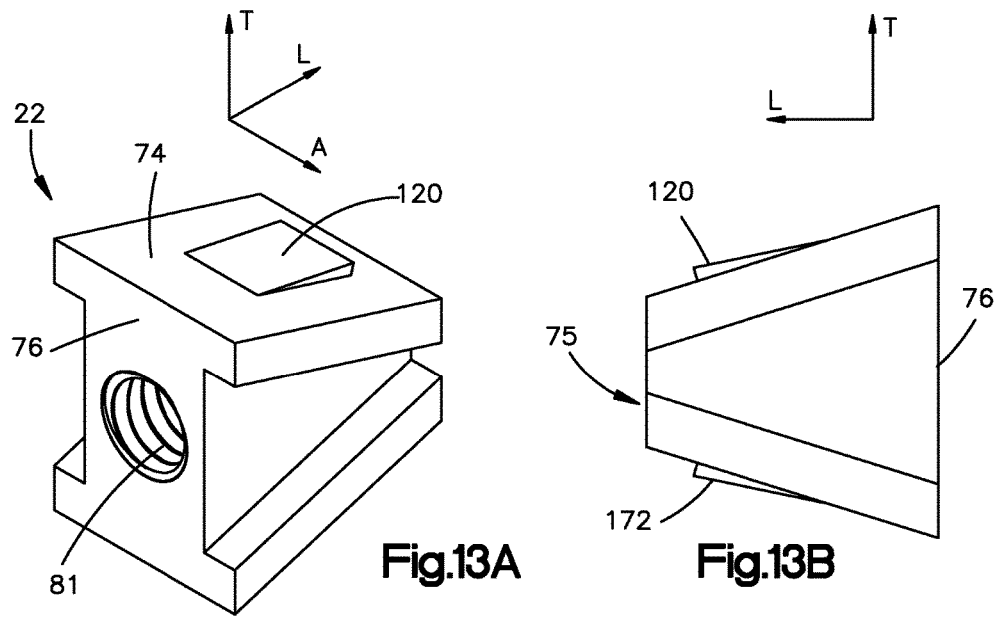
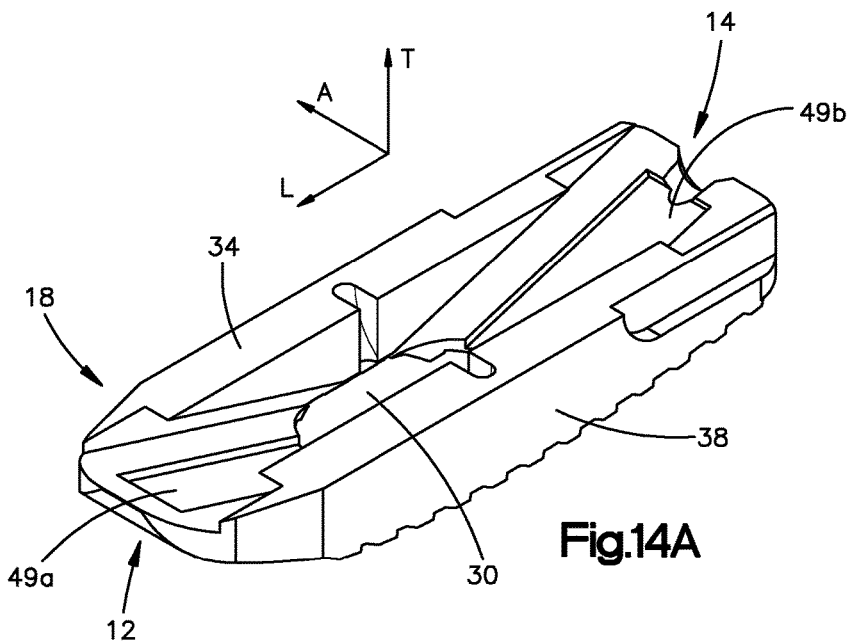

EXPANDABLE INTERVERTEBRAL IMPLANT, SYSTEM, KIT AND METHOD

TECHNICAL FIELD

The present invention relates to an expandable intervertebral implant, system, kit and method.

BACKGROUND

Removal of an intervertebral disc is often desired if the disc degenerates. Spinal fusion may be used to treat such a condition and involves replacing a degenerative disc with a device such as a cage or other spacer that restores the height of the disc space and allows bone growth through the device to fuse the adjacent vertebrae. Spinal fusion attempts to restore normal spinal alignment, stabilize the spinal segment for proper fusion, create an optimal fusion environment, and allows for early active mobilization by minimizing damage to spinal vasculature, dura, and neural elements. When spinal fusion meets these objectives, healing quickens and patient function, comfort and mobility improve. Spacer devices that are impacted into the disc space and allow growth of bone from adjacent vertebral bodies through the upper and lower surfaces of the implant are known in the art. Yet there continues to be a need for devices that minimize procedural invasiveness yet stabilize the spinal segment and create an optimum space for spinal fusion.

SUMMARY

According to one embodiment of the present disclosure, an expandable implant is configured for insertion into an intervertebral space that is defined between a first vertebral body and a second vertebral body. The implant can include a first bone contacting surface and a second bone contacting surface opposite the first bone contacting surface along a transverse direction. The implant can further include an insertion end and a trailing end opposite the insertion end along a longitudinal direction that is perpendicular to the transverse direction. The implant can further include first and second side surfaces opposite each other along a lateral direction that is perpendicular to both the transverse direction and the longitudinal direction. The implant can further include a first intermediate surface that extends between the first side surface and the first bone contacting surface, wherein the first intermediate surface is oblique to each of the first side surface and the first bone contacting surface. The implant can further include a second intermediate surface that extends between the second side surface and the second bone contacting surface, wherein the second intermediate surface is oblique to each of the first side surface and the first bone contacting surface. The first and second bone contacting surfaces can be movable away from each other from a collapsed configuration to an expanded configuration.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 2A is a perspective view of the implant shown in FIG. 1 in a collapsed configuration;

FIG. 2B is a perspective view of the implant shown in FIG. 1 in an expanded configuration;

FIG. 5A is a perspective view of a wedge member of the implant shown in FIG. 1;

FIG. 5B is a side view of the wedge member illustrated in FIG. 5A;

FIG. 5C is an end view of the wedge member illustrated in FIG. 5A;

FIG. 5D is another end view of the wedge member illustrated in FIG. 5A;

FIG. 6A is a perspective view of the actuation member of the implant shown in FIG. 1;

FIG. 6B is a side view of the actuation member of the implant shown in FIG. 1;

FIG. 6C is a perspective view of an actuation member in accordance with another embodiment of the present disclosure;

FIG. 7A is a sectional view of the implant of FIG. 2A taken along line 7A-7A, illustrating the implant in the collapsed configuration;

FIG. 7B is a sectional view of the implant of FIG. 2B taken along line 7B-7B, illustrating the implant in the expanded configuration;

FIG. 8A is a perspective view of an insertion tool used to insert the implant shown in FIG. 1 into an intervertebral space;

FIG. 8B is a perspective view of a tool engaged with the trailing end of the implant shown in FIG. 1;

FIG. 8C is a side view of a tool according to another embodiment of the present disclosure;

FIG. 8D is a partial perspective view of an implant supporting end of a tool shown in FIG. 8C;

FIG. 10B is a sectional side elevation view of the implant illustrated in FIG. 10A, shown in the collapsed configuration;

FIG. 10C is a sectional side elevation view of the implant illustrated in FIG. 10A, shown in the expanded configuration;

FIG. 11A is an end elevation view of the implant illustrated in FIG. 9A, shown inserted into an intervertebral space in a first orientation and in the collapsed configuration;

FIG. 11B is an end elevation view of the implant illustrated in FIG. 11A, but shown rotated from the first orientation to an intermediate orientation;

FIG. 11C is an end elevation view of the implant illustrated in FIG. 11B, but shown rotated from the intermediate orientation to a second orientation;

FIG. 11D is an end elevation view of the implant illustrated in FIG. 11C, but shown in the expanded configuration;

FIG. 12 is an exploded perspective view an implant according to another embodiment of the present disclosure;

FIG. 13A is a perspective view of a wedge member of the implant shown in FIG. 12;

FIG. 13B is a side view of the wedge member of the implant shown in FIG. 13A;

FIG. 14A is a perspective view of a plate of the implant shown in FIG. 12; and

DETAILED DESCRIPTION OF ILLUSTRATIVE EMBODIMENTS

Figure 1:
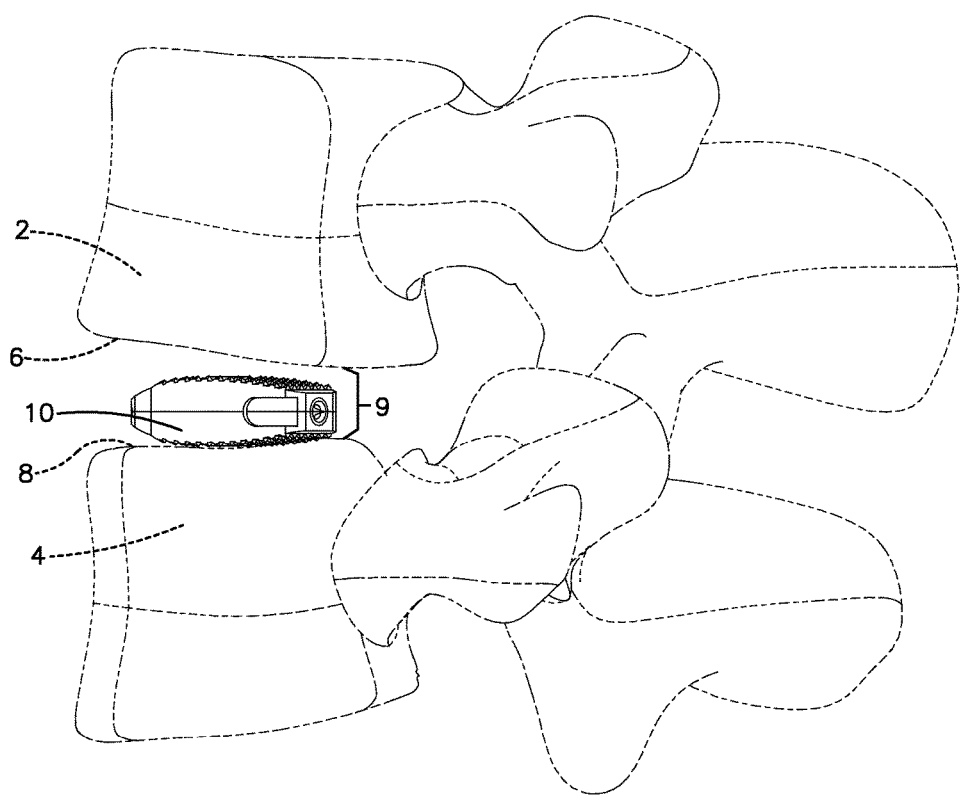
FIG. 1 illustrates an implant positioned between vertebral bodies, according to an embodiment of the present disclosure.

Referring to FIG. 1, a superior vertebral body 2 and an adjacent inferior vertebral body 4 defines an intervertebral space 9 extending between the vertebral bodies 2 and 4. The superior vertebral body 2 defines superior vertebral surface 6, and the adjacent inferior vertebral body 4 defines an inferior vertebral surface 8. The vertebral bodies 2 and 4 can be anatomically adjacent, or remaining vertebral bodies after a vertebral body has been removed from a location between the vertebral bodies 2 and 4. The intervertebral space 9 in FIG. 1 is illustrated after a discectomy, whereby the disc material has been removed or at least partially removed to prepare the intervertebral space 9 to receive an intervertebral implant or implant 10, as shown in FIGS. 2A-2B. The inserted and expanded implant 10 can achieve appropriate height restoration. The intervertebral space 9 can be disposed anywhere along the spine as desired, including at the lumbar, thoracic, and cervical regions of the spine.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The implant 10 is described herein as extending horizontally along a longitudinal direction "L" and a lateral direction "A", and transversely along a transverse direction "T". Unless otherwise specified herein, the terms "longitudinal," "lateral," and "transverse" are used to describe the orthogonal directional components of various implant components and implant component axes. The longitudinal direction L can be perpendicular to the transverse direction T. The lateral direction A can be perpendicular to the longitudinal direction L and the transverse direction T. It should be appreciated that while the longitudinal and lateral directions are illustrated as extending along horizontal directions, and that the transverse direction is illustrated as extending along a vertical direction, the directions may differ during use depending on the orientation of the implant. For instance, when the implant 10 is inserted into an intervertebral space, such as the intervertebral space 9, the transverse direction T extends transversely generally along the superior-inferior (or caudal-cranial) direction, while the horizontal plane defined by the longitudinal direction L and lateral direction A lies generally in the anatomical plane defined by the anterior-posterior direction, and the medial-lateral direction.

Figure 3:
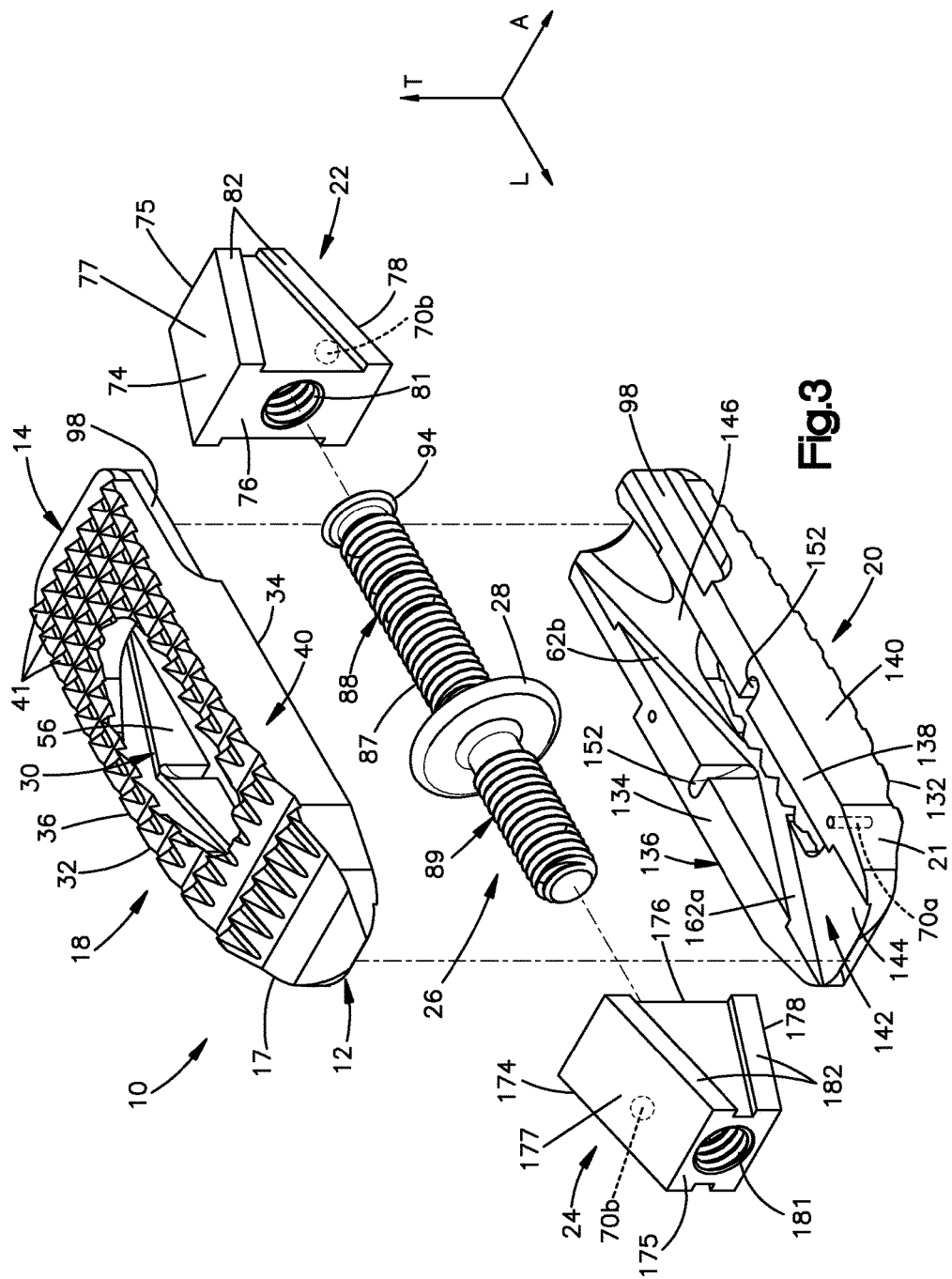
FIG. 3 is an exploded perspective view of the implant shown in FIG. 1.

Referring to FIGS. 1-3, the expandable intervertebral implant or implant 10 defines an implant body 13 that defines a distal or insertion end 12 and a proximal or trailing end 14 that is spaced from and opposite the insertion end 12 along an implant axis 1. The implant axis 1 can extend along the longitudinal direction L or any other linear or nonlinear direction as desired. The implant 10 is designed and configured to be inserted into an intervertebral space in a direction from the trailing end 14 toward the insertion end 12, also referred to herein as an insertion direction. The insertion direction can also be oriented along the longitudinal direction L. The trailing end 14 is configured to couple with one or more insertion instruments, which are configured to support and carry the implant 10 into the intervertebral space 9, and/or actuate the implant 10 from a collapsed configuration C shown in FIG. 2A into an expanded configuration E shown in FIG. 2B. The implant 10 can also extend between an upper or first bone-contacting surface 32 and a lower or second bone contacting surface 132 spaced from the first bone-contacting surface along the transverse direction T. The first and second bone contacting surfaces 32 and 132 are configured to engage the first and second vertebral bodies 2 and 4, respectively. Each of the first and second bone contacting surfaces 32 and 132 can be convex or partially convex, for instance, one portion of the surface is convex while another portion can be planar. The bone contacting surfaces 32 and 132 can also define a texture 41, such as spikes, ridges, cones, barbs, indentations, or knurls, which are configured to engage the vertebral bodies 2 and 4, respectively, when the implant 10 is inserted into the intervertebral space 9. The bone contacting surfaces 32 and 132 may be partially textured. For instance, the bone contacting surfaces 32 and 132 can include specific patterns of textured and non-textured portions. As used herein, the term "proximal" and derivatives thereof refer to a direction from the distal or insertion end 12 toward the proximal end 14. As used herein, the term "distal" and derivatives thereof refer to a direction from the proximal end 14 toward the insertion end 12. As used herein, the term "superior" and derivatives thereof refer to a direction from the bone contact surface 132 toward the first bone-contacting surface 32. As used herein, the term "inferior" and derivatives thereof refer to a direction from the upper or first bone-contacting surface 32 toward the lower or second bone contacting surface 132.

Continuing with FIGS. 1-3, the implant 10 includes a first or superior plate 18, a second or inferior plate 20 opposing the superior plate 18 along the transverse direction T, and a pair of wedge members. The pair of wedge members include a first wedge member 22 and a second wedge member 24 that couple to the superior plate 18 to the inferior plate 20. The first and second wedge members 22 and 24 are translatable along the longitudinal direction or the implant axis 1 so as separate the superior plate 18 from the inferior plate 20 along the transverse direction T. The implant 10 can include an actuation member 26 coupled to the first wedge member 22 and the second wedge member 24. The actuation member 26 has a flange 28 protruding from the actuation member 26 along the transverse direction T toward the superior plate 18 and the inferior plate 20. The superior plate 18 can define a first lumen 30 and the inferior plate 20 can define a second lumen 31 aligned with and opposite to the first lumen 30. The implant 10 is configured such that when the implant 10 is in the collapsed configuration C shown in FIG. 2A, a portion of first wedge member 22 and the second wedge member 24 are disposed at least partially in the first lumen 30 and the second lumen 31. The implant plates and/or wedge members can be formed of polyether ether ketone (PEEK) or any other suitable biocompatible polymeric material. The actuation member 26 can formed from a biocompatible polymeric material or metallic alloy, such as titanium or steel. It should appreciated that the any suitable material can be used to form the implant components as described herein. For instance, an entirety of the implant can be made from a titanium alloy. For instance, an entirety of the implant can be made from a titanium-aluminium-niobium (TAN) alloy.

Figure 4A:
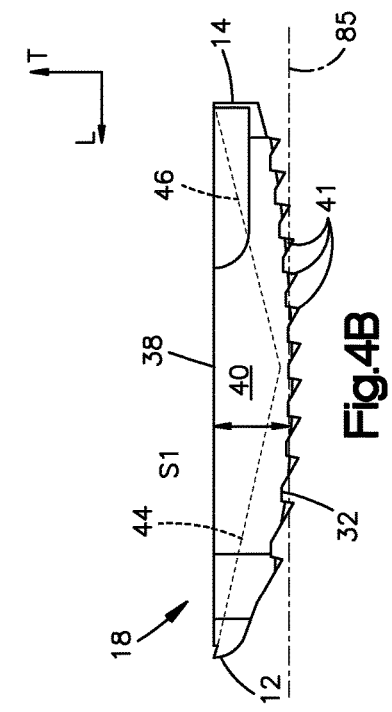
FIG. 4A is a perspective view of the interior surface of a plate of the implant shown in FIG. 1.
Figure 4B:
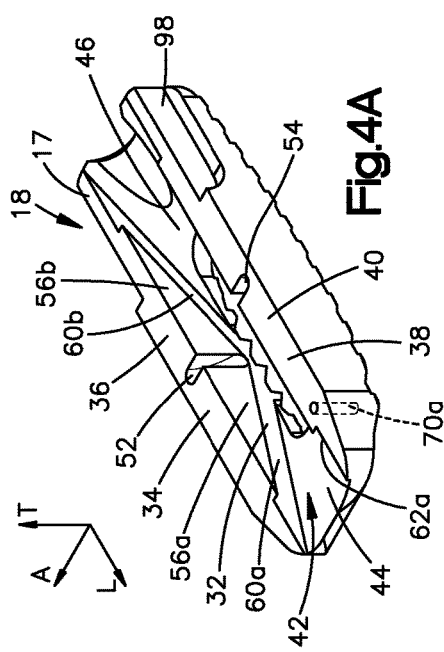
FIG. 4B is side view of a plate of the implant shown in FIG. 4A.
Figure 4C:
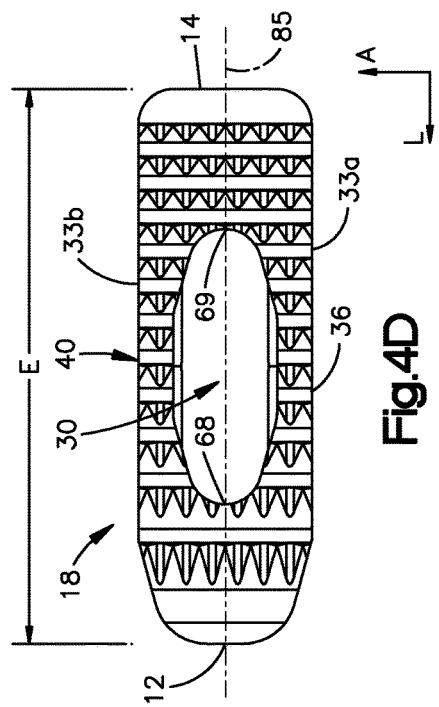
FIG. 4C is a bottom plan view of a plate of the implant shown in FIG. 4A.
Figure 4D:
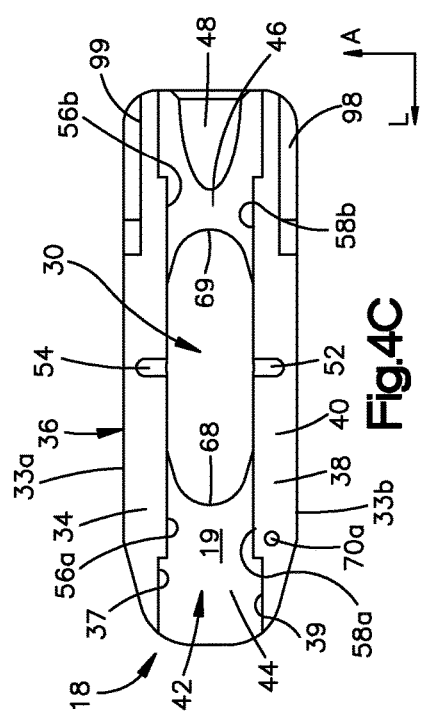
FIG. 4D is a top plan view of the plate of the implant shown in FIG. 4C.

Referring to FIGS. 3-4D, the superior plate 18 is configured for coupling with the first wedge member 22, the second wedge member 24, and at least a portion of the actuation member 26, for support on the flange 28. The superior plate body 17 can define a cavity 42 configured to carry the first and second wedge members 22 and 24 are the actuation member 26. The superior plate 18 defines a first or superior plate body 17 that extends between the insertion end 12 and the trailing end 14 along the longitudinal direction L. The superior plate body 17 defines the first bone-contacting surface 32, and first and second interior plate contact surfaces 34 and 38 spaced from the bone-contacting surface 32 along the transverse direction T. The superior plate body 17 also defines first and second ramp surfaces 44 and 46 spaced from the bone contacting surface 32 along the transverse direction T. The superior plate body 17 further defines a first side surface 33a and a second side surface 33b opposite the first side surface 33a. The first and second side surfaces 33a and 33b extend between the bone-contacting surface 32 and respective interior plate contact surfaces 34 and 38 along the transverse direction T. The plate body 17 also defines a first transverse surface 37 and a second transverse surface 39 that extend from the ramp surfaces 44 and 46 to respective interior plate contact surfaces 34 and 38 along the transverse direction T. The plate body 17 thus defines a first sidewall 36 and a second sidewall 40 spaced from the first sidewall 36 along the lateral direction A. Specifically, the first sidewall 36 defines the first side surface 33a and the first transverse surface 37 that is spaced from the first side surface 33a along the lateral direction A. The first sidewall 36 further defines the first interior plate contact surface 34 that is spaced from the first and second ramp surfaces 44 and 46 along the transverse direction T. The second sidewall 40 defines the second side surface 33b and the second transverse surface 39 that is spaced from the second side surface 33b along the lateral direction A. The second sidewall 40 further defines the second interior plate contact surface 38 that is spaced from the first and second ramp surfaces 44 and 46 along the transverse direction T. As illustrated, the cavity 42 extends along the longitudinal direction L of the plate body 17 and along the lateral direction A between the opposed first and second sidewalls 36 and 40. The first lumen 30 is in communication with the cavity 42 as detailed below. In the embodiment shown, the first and second sidewalls 36 and 40 converge with the bone contacting surface 32 to form a tapered insertion end 16 (FIG. 2A).

Continuing with FIGS. 3-4D, the first and second sidewalls 36 and 40 are configured to couple to the first and second wedge members 22 and 24. The first sidewall 36 can define at least one slot, for instance a first slot 52 for receiving a portion of the flange 28 of the actuation member 26. The first slot 52 is disposed in the first sidewall 36 at a location between the insertion end 12 and the trailing end 14 of the plate body 17. The second sidewall 40 can define at least one or second slot 54 for receiving another portion of the flange 28 of the actuation member 26. The second slot 54 is disposed in the first sidewall 36 at a location between the insertion end 12 and the trailing end 14 of the plate body 17. The second slot 54 is aligned, for instance laterally aligned, with and opposing the first slot 52 such that each slot 52 and 54 is positioned to receive a portion of the flange 28. The first and second slots 52 and 54 are also configured to mate with the structure of the flange 28. For instance, the first and second slots have an inner profile that is curvilinear and corresponds to the curvilinear profile of the flange 28. In other alternate embodiments, the first and second slots 52 and 54 may have a rectilinear shape. It should be appreciated that the slots 52 and 54 may have any desired shape that can slidingly receive a portion of the flange 28. For example, if the flange 28 has a square profile, the slots 52 and 54 can be configured to mate with the square shaped flange. In alternate embodiments, the first and second wall 36 and 40 can include a plurality of spaced slots spaced apart along the longitudinal direction L and disposed on the first and second sidewalls 36 and 40 to receive a corresponding number of flanges or flanges portions protruding from the actuation member 26. For example, the first and second walls may include slots 52 and 54, and additional slots 52L and 54L (not shown) spaced apart from the slots 52 and 54 along the longitudinal direction (the longitudinal direction L).

The plate body 17, or for instance the first and second sidewalls 36 and 40, can define one or more projections 56 and 58 that protrude from respective first and second inner surfaces of the first and second sidewalls 36 and 40 along the lateral direction A. The inner surfaces of the sidewalls 36 and 40 are opposite the respective first and second side surfaces 33a and 33b. The projections 56 and 58 are configured to engage a portion of the first and second wedge members 22 and 24 as further detailed below. In particular, the first sidewall 36 can define a first set of projections 56 that extend from the first inner surface of the first sidewall 36 along the lateral direction A into the cavity 42. The first set of projections 56 can include a first wall projection 56a and a second wall projection 56b spaced proximally from the first wall projection 56a along the longitudinal direction L. In the illustrated embodiment, the first slot 52 separates the first wall projection 56a from the second wall projection 56a. The second sidewall 40 can define a second set of wall projections 58 that extend from the second inner surface of the second sidewall 40 along the lateral direction A into the cavity 42. The second set of projections 58 can include a third wall projection 58a and a fourth wall projection 58b spaced proximally from the third projection 58a along the longitudinal direction L. In the illustrated embodiment, slot 54 separates the third wall projection 58a from the fourth wall projection 58b. While each wall 36 and 40 is illustrated has having two projections, each wall 36 and 40 can have a single projection, or more than two projections.

The plate body 17, for instance the first and second sidewalls 36 and 40, can further define set of inclined connection grooves 60 and 62 configured to receive a portion of the first and second wedge members 22 and 24. The wall projections 56 and 58 protrude from respective walls 36 and 40 along the lateral direction A, as discussed above. The wall projections 56 and 58 are also spaced from the respective first and second ramp surfaces 44 and 46 along the transverse direction T to define the sets of inclined connection grooves 60 and 62. The first set of projections 56a and 56b extend from the first sidewall 36 so as to define first and second inclined connection grooves 60a and 60b respectively (FIG. 4A). The second connecting groove 60b is proximal disposed relative to the first connection groove 60a. The slot 52 is disposed between the first and second inclined connection grooves 60a and 60b. The second set of projections 58a and 58b extend from the first wall 40 to define third and fourth inclined connection grooves 62a and 62b, respectively. The fourth connection groove 62b is proximal to the third inclined connection groove 62a. The slot 54 is disposed between the inclined connection grooves 62a and 62b. The first and third projections 56a and 58a can also be referred to as the distally positioned projections, while the second and fourth projections 56b and 58b can be referred to as proximally positioned projections. Further, the first and third inclined connection grooves 60a and 62a can be referred to as the distally positioned connection grooves, while the second and fourth inclined connection grooves 60b and 62b can be referred to as the proximally positioned connection grooves.

Each opposing inclined connection grooves 60 and 62 extends from the lumen 30 toward the opposing implant or implant ends 12 and 14 along the longitudinal direction L. The plate body 17 can define a lumen first perimeter portion 68 and an opposing lumen second perimeter portion 69 that is spaced from the first perimeter portion 68 along the first lumen axis 85. Lumen perimeter portion 69 is disposed proximally toward the trailing end 14 of the implant 10 and lumen perimeter portion 68 is disposed distally toward the insertion end 12 of the implant 10. The distally positioned grooves 60a and 62a extend distally from the first perimeter portion 68 of the lumen 30 toward the plate insertion end 12, while the proximally positioned grooves 60b and 62b extend proximally from the second perimeter portion 69 of the lumen 30 toward the trailing end 14. The inclined connection grooves 60 and 62 can thus slidably receive therein the ridges 82 and 182 of the first and second wedge members 22 and 24.

Continuing with FIGS. 3-4C, the plate body 17 defines ramp surfaces 44 and 46, for instance a first ramp surface 44 and a second ramp surface 46 that are configured to mate with and slide along portions of the first and second wedge members 22 and 24. The first ramp surface 44 extends from the first perimeter portion 68 of the lumen 30 distally generally along the longitudinal direction L to the insertion end 12. The ramp surface 44 is inclined to abut and slidingly receive a portion of the second wedge member 24. The second ramp surface 46 extends from the second perimeter portion 69 of the lumen 30 proximally along the longitudinal direction L toward the trailing end 14. The ramps surfaces 44 and 46 also extend laterally along the lateral direction A between the opposing first and second plate walls 36 and 40. Each ramp surface 44 and 46 can define a ramp angle β (not shown) defined with respect to interior plate contact surfaces 34 and 38. It should be appreciated that the angle β can vary as needed. The plate body 17 can also define a curvilinear portion 48 disposed at the trailing end 14 of the plate body 17 and in communication with the second ramp surface 46. The curvilinear portion 48 is configured align with a corresponding curvilinear portion 148 on the inferior plate 20. When the plates 18 and 20 are in the collapsed configuration as shown in FIGS. 2A and 7A, the curvilinear portions 48 and 148 define an access opening 50. The access opening 50 that provides access the actuation member 26, as further detailed below.

Continuing with FIGS. 3-4D, the superior plate 18 can include one or more radiographic markers. The plate body 17 can define one or more bores (not shown) sized and dimensioned to receive a radiographic marker 70a therein. As illustrated, the radiographic marker 70a is disposed in the second sidewall 40 and positioned toward insertion end 12 of the plate 18. The opposing plate 20 can have a radiographic marker 170a as well. When the implant 10 is inserted into the intervertebral space 9, and the implant 10 is expanded from the first configuration C to the expanded configuration E, the markers 70a and 170a can separate along the transverse direction T. With image analysis, the extent of plate separation can be determined or indicated by observing the extent of separation between the markers 70a and 170a disposed in the superior plate 18 compared to marker disposed in the inferior plate 20.

The inferior plate 20 is configured similarly to the superior plate 18. The inferior plate 20 thus includes similar structural features that correspond to the structural features described above with respect to the superior plate 18. The inferior or second plate 20 defines a plate body 21 that extends between the insertion end 12 and the trailing end 14 along the longitudinal direction L. The inferior plate body 21 defines a second bone contacting surface 132, first and second interior plate contact surfaces 134 and 138 spaced from the bone contacting surfaces 32 along the transverse direction T, and first and second ramp surfaces 144 and 146 spaced from the bone contacting surfaces 32 along the transverse direction T. The inferior plate body 21 therefore defines define cavity 142, first and second sidewalls 136 and 140, a first set of projections 156a-b, a second set of projections 158a-b, and inclined connection grooves 160a-b, 162a-b.

The inferior plate body 21 further defines a first side surface 133a and a second side surface 133b opposite the first side surface 133a. The first and second side surfaces 133a and 133b extend between the second bone-contacting surface 132 and the first and second interior plate contact surfaces 134 and 138 along the transverse direction T. The inferior plate body 21 also defines a first transverse surface 137 and a second transverse surface 139 that extend from the ramp surfaces 144 and 146 to respective first and second interior plate contact surfaces 134 and 138 along the direction V. The plate body 21 thus defines the first sidewall 136 and the second sidewall 140 that is spaced from the first sidewall 136 along the lateral direction A. Specifically, the first sidewall 136 defines the first side surface 133a and the first transverse surface 137 that is spaced from the first side surface 133a along the lateral direction A. The first sidewall 136 further defines the first interior plate contact surface 134 that is spaced from the first and second ramp surfaces 144 and 146 along the transverse direction T. The second sidewall 140 defines the second side surface 133b and the second transverse surface 139 that is spaced from the second side surface 133b along the lateral direction A. The second sidewall 140 further defines the second interior plate contact surface 138 that is spaced from the first and second ramp surfaces 144 and 146 along the transverse direction T. As illustrated, the cavity 142 extends along the longitudinal direction L of the plate body 21 and along the lateral direction A between the opposed first and second sidewalls 136 and 140. In the embodiment shown, the first and second sidewalls 136 and 140 converge toward the bone contacting surface 132 to form a tapered insertion end 16.

The first and second interior plate contact surfaces 134 and 138 of the inferior plate 20 are configured to oppose and contact the first and second interior contact surfaces 34 and 38, respectively, of the superior plate 18. The superior plate 18 and inferior plate 20 can define opposing indentations 98 and 99 at the trailing end 14 of the implant 10. The indentations 98 and 99 are configured to receive a portion of an insertion tool 100 and 300 (FIG. 8A-8F). Further, the first side surface 33a and the first side surface 133a can be disposed at a first side of the implant, and the second side surface 33b and the second side surface 133b can be disposed at a second side of the implant opposite the first side with respect to the lateral direction A. For instance, the first side surface 33a and the side first surface 133a can be inline with each other along the transverse direction T, and the second side surface 33b and the second side surface 133b can be inline with each other along the transverse direction T.

The first and second plates 18 and 20 can also define the respective first and second lumens 30 and 31 as discussed above. Each lumen 30 and 31 has been configured to receive at least a portion of the first and second wedge members 22 and 24 to maximize the compact design and the expansion characteristics of the implant 10. The lumens 30 and 31 partially receiving portions of the first and second wedge members 22 and 24 when the implant 10 is in the collapsed configuration C (FIG. 2A), which allows for the dimensions of the first and second wedge members 22 and 24 to be increased over wedge members used in implants with lumens not configured to permit a portion of the wedge member to extend therethrough. Further, the configured first and second wedge members 22 and 24 can improve implant 10 stability when expanded. Thus, the implant 10 has a collapsed configuration that is compact and less invasive, and an expanded configuration that is dimensionally stable. The lumens 30 and 31 have the additional benefit of promoting bone growth when implanted in the intervertebral space 9. The first lumen 30 and second 31 are generally elongate in the longitudinal direction L. The lumens 30 and 31 can have other shapes, for instance the lumens can be circular (FIGS. 9-11B). The lumen 30 extends through the superior plate body 17 along the transverse direction T into communication with the cavity 42. Likewise, the second lumen extends through the second or inferior plate body 21 into communication with the cavity 142. The superior plate body 17 can define a lumen axis 85 that extends along the longitudinal direction L of plate body 17. The lumen axis 85 is aligned with the bone-contacting surface 32 or at leady portion thereof, for instance the lumen axis 85 is spaced from the implant axis 1 along the transverse direction T with a portion of the bone-contacting surface 32. The plate body 17 can also define a lumen first perimeter portion 68 and an opposing lumen second perimeter portion 69 that is spaced from the first perimeter portion 68 along the first lumen axis 85. Lumen perimeter portion 68 is disposed proximally toward the implant trailing end 14 and lumen perimeter portion 69 is disposed distally toward the implant insertion end 12. Likewise, the inferior plate body 21 can define a second lumen axis 85a (not shown) that extends along the longitudinal direction L of plate body 21 and is aligned along the transverse direction T with bone contacting surface 132. The plate body 21 can also define a lumen first perimeter portion 168 and an opposing lumen second perimeter portion 169 that is spaced from the first perimeter portion 168 along the second lumen axis 85a. Lumen perimeter portion 168 is disposed proximally toward the trailing end 14 and lumen perimeter portion 169 is disposed distally toward the implant insertion end 12.

Referring to FIGS. 3, 5A-5D, the first wedge member 22 and the second wedge member 24 are configured for slidable coupling to the superior and inferior plates 18 and 20. The first and second wedge members 22 and 24 are configured similarly, and for illustrative purposes, only the first wedge member 22 will be described below. The first wedge member 22 defines a wedge body 74 extending along a wedge axis 3 between a narrow end 75 and an inner end 76 spaced from the narrow end 75. The wedge axis 3 is generally aligned with the implant axis 1 and extends along the longitudinal direction L. As show in FIGS. 3 and 7A, the first wedge narrow end 75 is positioned toward the outer or trailing end 14 of the implant 10, while the inner end 76 is positioned to face the distal or insertion end 12 of the implant 10. Further, the second wedge member 24 has a wedge body 174 that extends from a narrow end 175 to an inner end 176 along the wedge axis 3, wherein the narrow end 175 is positioned toward the distal or insertion end 12 of the implant 10 and the inner end 176 is positioned toward the proximal or trailing end 14 of the implant. Thus, the first wedge member 22 is positioned such that the inner end 76 of the first wedge member 22 and faces the inner end 176 of the second wedge member 24.

The body 74 defines a superior tip 76s spaced from an inferior tip 76i along a transverse direction T and disposed at the inner end 76. A first or inner wedge dimension H1 is defined as the distance between the superior and inferior tips 76s and 76i along the transverse direction T. The plate body 17 can define first plate dimension L51 extending between the bone contacting surface 32 and the interior contact surfaces 34 and 38, while the plate body 21 can define a second plate dimension 52 extending between the bone contacting surface 132 and the inner surfaces 134 and 138. In an embodiment, the first or inner wedge dimension H1 is about twice the distance of the first plate dimension S. In an embodiment, the first or inner wedge dimension H1 can be greater than or equal to the sum of the first plate dimension S and the second plate dimension 52. In an embodiment, the first or inner wedge dimension H1 can be less than or equal to sum of the first plate dimension S1 and second plate dimension 52.

The body 74 defines a wedge shape configured for slidable coupling to the first and second plates 18 and 20. The body 74 defines a first or superior inclined surface 77 and a second inclined or inferior inclined surface 78 opposite the first incline surface 77. The first and second inclined surfaces 77 and 78 extend along the longitudinal direction L from the inner end 76 toward the narrow end 75. The first inclined surface 77 is angularly offset from a second inclined surface 78. In an embodiment, the first and second inclined surfaces form an angle θ defined between intersecting lines coincident with the first and second inclined surfaces 77 and 78 (FIG. 5B). Angle θ can vary as needed. The first inclined surface 77 can slidably mate with a ramp surface 46 on an interior the superior plate 18, while the second inclined surface 78 can slidably mate with a first ramp surface 146 on of the inferior plate 20. The body further defines a first side 79 and a second side 80 opposite the first side 79. The first and second sides 79 and 80 extend along the longitudinal direction L between the inner end 76 and the narrow end 75, and transversely along the transverse direction T between the first and second inclined surfaces 77 and 78.

The first wedge member 22 also includes one or more ridges 82 (82a-d) protruding from the body 74 along the lateral direction A. The ridges 82 are configured to couple the first wedge member 22 to the superior plate 18 and inferior plate 20. For instance, the one or more ridges 82 are slidably coupled to respective portions of the inclined connections grooves 60, 62 160, 162. Each ridge 82a-82d extends between the narrow end 75 and the inner end 76 of the body 74 generally along the wedge axis 3. Ridges 82a-82d also extend along the respective first and second inclined surfaces 77 and 78. Ridges 82a and 82c are angled only offset action angle with respect to ridges 82b and 82d. The transversely spaced apart ridges 82c and 82d disposed on the first side 79 of the body 74 can define a recess portion 86 which can receive the distally oriented projections 56b and 156b of the plates 18 and 20, respectively. The transversely spaced apart ridges 82a and 82b are disposed on the side 80 define recess portion 84 which receives the distally oriented projections 58b and 158b of the plate 18 and 20. The laterally spaced apart ridges 82a and 82c are received in the inclined connection grooves 60b and 62b of the superior plate. The other laterally spaced apart ridges 82b and 82d are received in the inclined connection grooves 160b and 162b of the inferior plate 20 (FIG. 3).

The wedge member body 74 also defines first bore 81 extending through the body 74 between the narrow end 75 and the inner end 76 along the wedge axis 3. The first bore 81 is configured to receive at least a portion of the actuation member 26. In an embodiment, the bore 81 is internally threaded to mate with a corresponding threaded portion of the actuation member 26. Further, the wedge member body 74 includes an additional bore or receiving a radiographic marker 70b therein.

The second wedge member 24 is configured similarly to the first wedge member 22. The second wedge member 24 defines a second body 174. The body 174 defines a narrow end 175 spaced apart from an inner end 176 along the wedge axis 3, first and second inclined surfaces 177 and 178, a plurality of ridges 182 extending from body 174, and a second bore 181 extending through the body 174 between the narrow and inner ends 175 and 176. The first and second sides 179 and 180 extend between the inclined surfaces 177 and 178. The body 174, for instance the body inner end 176 defines a superior tip 176, spaced apart from an inferior tip 176i along a transverse direction T. The second wedge member has a wedge dimension H2 (not shown) defined as the distance between the superior tip 176s and the inferior tip 176i. H2 can be equal to H1. As shown in FIG. 3, the second wedge member 24 is spaced apart from the first wedge member 22 along the longitudinal direction L such that the inner end 175 of the second wedge member 24 faces the inner end 75 of the first wedge member 22. The second wedge member 24 also includes ridges 182a-182d that are similar to ridges 82a and 82d.

Continuing with FIGS. 6A-6C, the actuation member 26 is configured to couple the first and second wedge members 22 and 24 together while also providing stability to the superior plate 18 and inferior plate 20 during implant expansion. The actuation member 26 extends along the longitudinal direction L between a distal end 27i and a proximal end 27e. The actuation member 26 defines a shaft 87 extending between the opposed ends 27i and 27e. The shaft 87 can be threaded. For instance, the shaft 87 can define exterior threads. The flange 28 protrudes from the shaft 87 along the lateral A or a radial direction R. The flange 28 defines a flange body 28b, a distal facing surface 29d and a proximal facing surface 29p spaced from the distal facing surface 29d along the longitudinal direction L. The flange body 28b is sized and dimensioned to slide within the slots 52 and 54 of plate 18, and slots 152 and 154 of the plate 20.

The radial direction R can be aligned with the lateral direction A and the transverse direction T and is used to indicate that the flange 28 protrudes radially from the shaft 87. The flange 28 can have other configurations, and as such Cartesian coordinates may better indicate directional components.

The shaft 87 can define a first threaded portion 88 disposed proximally relative to the flange 28, and a second threaded portion 89 disposed distally from the flange 28. The first shaft portion 88 can have a length L1 extending from the flange proximal face 29p to the proximal end 27e, and the second threaded portion 89 has a second length L2 extending from the flange distal face 29d to the distal end 27i, wherein the first length L1 is greater than the second length L2. The shaft 87 is configured to extend through the bore 81 of the first wedge member 22 and into the curvilinear portions 48 and 148 or access opening 50 of the plates. The first threaded portion 88 has a thread pattern that is oriented in the opposite direction of the thread pattern formed on the second threaded portion 89. The internal threads of the first and second bores 81 and 181 are in opposing orientations such that when the actuation member 26 rotates, the first and second wedge members 22 and 24 translate along the actuation member 26 toward each other or away from each depending on the rotation direction of the actuation member 26. The thread pattern on each portion may have the same pitch such that the first and second wedge members 22 and 24 can translate along the actuation member 26 at the same rate. The thread pitch can be different if needed when different distraction profiles are desired in the expanded configuration (e.g. kyphotic or lordotic). The proximal end 27e of the actuation member 26 can define a lip 94 configured to abut the narrow end 75 of the first wedge member 22. The lip 94 and can help prevent displacement of the actuation member 26 from the first wedge member 22. The proximal end 27e of the actuation member 26 can define a socket 90 configured to receive or support a portion of an instrument, as further detailed below. The socket 90 can have any configuration as need to receive an instrument, such as hex, Phillips, flat, star, etc.

The actuation member 28 can further include a protective shroud 43 that surrounds at least a portion of the flange 28. For instance, the protective shroud 43 can include an inner wall 43a that faces the flange 28, and an outer wall 43b that is opposite the inner wall 43a. The inner wall 43a can define an opening 45 that extends into the shroud 43 in the lateral direction A, and has a laterally open end 47. Thus, the flange 28 can be inserted into the open end 47 and into the opening along the lateral direction A. The shroud 43 can define a rectangular cross section, or any suitable alternative cross section as desired. The shroud 43 can be dimensioned so as to fit between the first and second wedges 22 and 24 and into the implant plates 18 and 20 as described above with respect to the flange 28. Thus, the flange 28 can be rotatable in the shroud 43 during operation. Alternatively, the shroud 43 can be removed from the flange 28 along the lateral direction A prior to insertion of the flange 28 between the first and second wedges 22 and 24.

The implant 10 as described herein can have initial dimensions and expanded dimensions. For, instance, the implant can have first implant height D1 defined between opposing portions 11a and 11b of the first and second bone contacting surfaces 32 and 132, and second implant height D2 defined between opposing portions 11a and 11b of the first and second bone contacting surfaces 32 and 132 when the implant is expanded (FIGS. 2A and 2B). In an embodiment, the first and second bone contacting surfaces 32 and 132 can define a dimension in the lateral direction A as desired, such as between 8 mm and 12 mm. In an embodiment, the first implant height D1 can range between 7 mm and 15 mm, such as between 7 mm and 10 mm, and the second expanded height can range between 10 mm and 20 mm, such as between 10 mm and 13 mm. Thus, the opposed superior and inferior plates can be spaced apart any distance as desired, such as between 3 mm and 5 mm, when the implant is expanded. For instance, in an embodiment, the first height can be 7 mm while the expanded, second height can be 10 mm. In another embodiment, the first height can be 9 mm and the expanded, second height D2 can be 13 mm. Other dimensions are possible as well. For example first heights can be up to 7 mm, 9 mm, or greater. The implant 10 can have length E defined between the distal or insertion end 12 and the proximal or trailing end 14. The length E can range between 24 mm and 32 mm. The length E, however, can be shorter than 24 mm or greater than 32 mm. Further, the implant is configured such the length E of the implant 10 is consistent regardless of when the implant 10 is in the collapsed configuration or when the implant 10 is in the expanded configuration. That is, the first and second wedge members 22 and 24 are configured such the opposed narrow ends 75 and 175 translate to, but do not protrude from the implant trailing end 14 or implant insertion end 12 when in the expanded configuration. This configuration improves implant stability.

Referring to FIGS. 8A-8B, the system as described herein includes one or more insertions tools. An insertion tool 100 can include a handle 105 and a shaft 104 extending from the handle toward an implant supporting end 107. The implant supporting end 107 is configured to support, for instance carry or engage with a portion of the implant 10. The implant supporting end 107 can include spaced apart tabs 101 and 102 configured and sized to be received in the implant indentations 98 and 99. When the implant tabs 101 and 102 engage the indentations 98 and 99, the tool 100 can position and/or insert the implant 10 into the intervertebral space 9. An additional tool 350 can be used to expand the implant 10 from the collapsed configuration to the expanded configuration. The tool 350 can include a handle 355 and a shaft 354 extending from the handle toward an implant supporting end 357. The implant supporting end 357 is configured to engage the actuation member 26, such that rotation of the tool 350 can cause rotation of the actuation member 56.

Figure 8E:
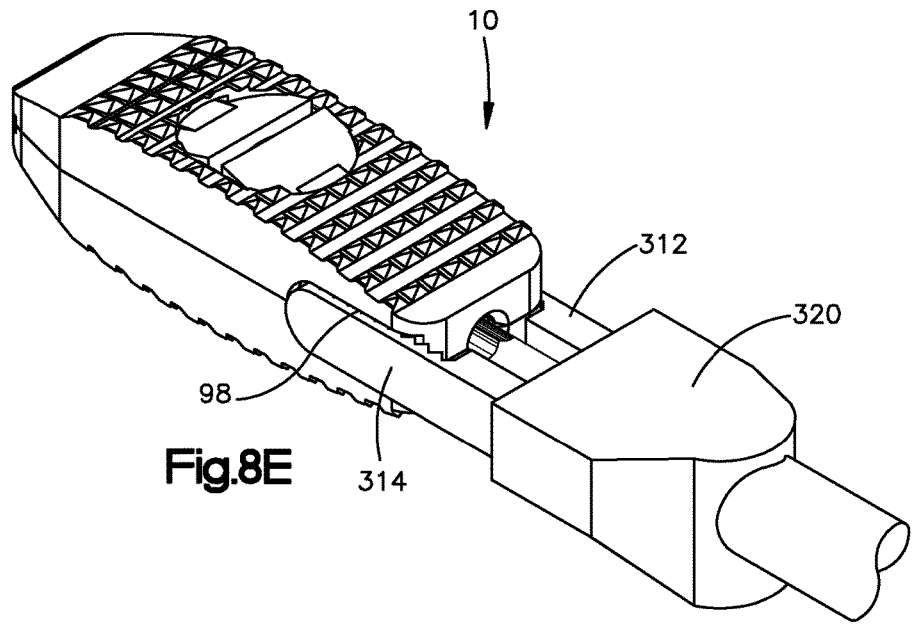
FIG. 8E is a partial perspective view of the tool shown in FIG. 8D supporting an implant.
Figure 8F:
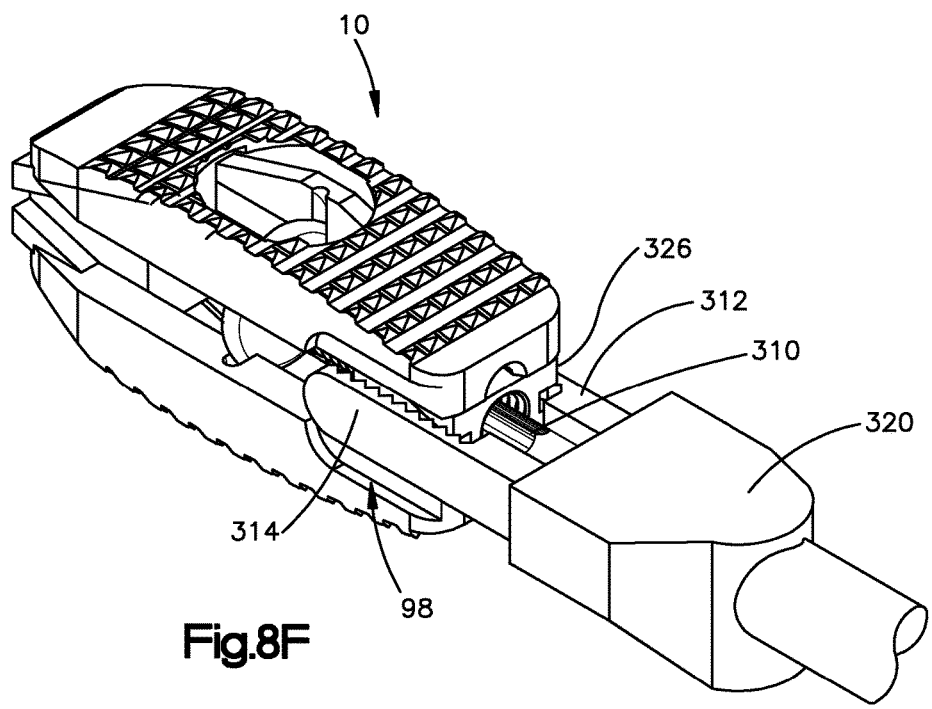
FIG. 8F is another partial perspective view of the tool shown in FIG. 8E.

Referring to FIGS. 8D-8E, another embodiment a tool 300 can include a handle 302, tool housing 304 connected to the handle 302, and an elongate cannualated shaft 306 extending from the housing 304 toward an implant supporting end 307. The housing 304 and cannualated shaft 306 are elongate along an insertion tool axis 301. The housing 304 and cannualated shaft 306 define a cannulation (not shown) that extends through the housing 304 and shaft 306. The tool 300 also includes rotation member 318 that defines a rotation member 316 and an elongate rod 308 that extends from the rotation member 318 toward an engagement end 310 along the axis 301 as shown in FIG. 8D. The rotation member 318 is rotatable in the cannulation as well as slidable or translatable in the cannulation along the tool axis 301. The tool implant supporting end 307 includes a body 320 and tabs 312 and 314 extending from the body. The engagement end 310 of the rod 308 protrudes from the body 320 and is disposed between the tabs 312 and 314. Tool 300 can be used to clasp, insert, and then expand the implant. The tool 300 can be used clasp the implant 10 by inserting the tabs 312 and 314 into the indentations 98 and 99 while the rotation member 318 can be slide into engagement with the actuation member 26. For instance, the engagement end 310 can be coupled to the opening 90 in the actuation member 26 while tabs 312 and 314 support the implant 10. The rotation member 318 can be rotated relative to the shaft 306 so that the actuation member 26 is rotated.

Referring to FIGS. 7A and 7B, implant 10 is configured to expand from the collapsed configuration C (FIG. 7A) to the expanded configuration E (FIG. 7B). When the first or collapsed configuration C, the first and second wedge members 22 and 24 are disposed in the implant such that the inner ends 76 and 176 face and are spaced apart from each other to define a gap therebetween. The actuation member 26 is coupled to the first and second wedge members 22 and 24 such that the first threaded portion 88 is disposed in the first bore 81 and the second threaded portion 89 is disposed in the second bore 181. The flange 28 extends between (in the sup) and along the opposed inner ends 76 and 176 of the first and second wedge members 22 and 24. The inclined surfaces 77 and 78 are adjacent to opposing plate ramp surfaces 46 and 146, while the second wedge member 24 inclined surfaces 177 and 178 are adjacent to opposing plate ramp surfaces 44 and 144. The inner end superior tips 76s and 176s extend into the lumen 30 and an into a plane containing the bone contacting surface 32, while the inner end tips 76i and 176i extend into the second lumen and to a plane containing the bone contacting surface 132. The flange distal face 29d abuts the inner end 176 of the second wedge member 24, while the flange proximal face 29p abuts the inner end 76 of the first wedge member 22. Portions of the first and second wedge members 22 and 24, for instance tips 76s-i and 176s-i, disposed in the lumens 30 and 31 allows for a wedge profile that aids plates 18 and 20 separation with relatively little advancement of the first and second wedge members 22 and 24 along the actuation member 26. For instance, the superior tips 76s and 176s extend to, for instance traverse, the first lumen axis 85 such that the tips are generally aligned with the bone contact surface 32 of the superior plate 18. The inferior tips 76i and 176i extend to, for instance traverse, the second lumen axis 85a such that the tips 76i and 176i are generally aligned with the bone contact surface 132 of the inferior plate 20.

Turning to FIGS. 7B and 8A-8F, when the actuation member 26 is rotated for via a tool 150 or 350, the first threaded portion 88 of the actuation member 26 causes the first wedge member 22 to translate toward the trailing end 14 of the implant 10. The inclined surfaces 77 and 78 bears against the ramp surfaces 46 and 146 to separate the superior plate 18 from the inferior plate 20 along the transverse direction. The ridges 82a-d slide along inclined connection grooves 60b, 160b, 62b, 162b (not shown in the FIG. 7B). While the first wedge member 22 is translating toward the implant trailing end 14, the second threaded portion 89 of the actuation member 26 engages the second bore 181 and causes the second wedge member 24 to translate toward the insertion end 12 of the implant 10. The inclined surfaces 177 and 178 of the second wedge member 24 slide along the ramp surfaces 44 and 144, so as to separate the superior plate 18 from the inferior plate 20 along the transverse direction T. The ridges 182a-182d slide along respective inclined connection grooves 60a, 160a, 62a, 162a (not shown in the FIG. 7B). The flange 28 remains disposed in the slots 52, 54, 152, 154 during actuation of the implant 10 and provides additional stability against sheer when the implant 10 is expanded. The embodiment shown in FIGS. 7A and 7B illustrate the superior plate 18 separating from the inferior plate 20 along a transverse direction T while remaining generally parallel to each other. In other alternate embodiments, the implant can be configured to such that a lordotic or kyphotic distraction is achieved. For example, the threaded portions of the actuation member can be configured to cause one wedge member to translate at a faster rate compared to the other wedge member. In such an embodiment, when the implant 10 is expanded, the superior plate 18 will be angularly offset from the inferior plate 20.

Figure 9A:
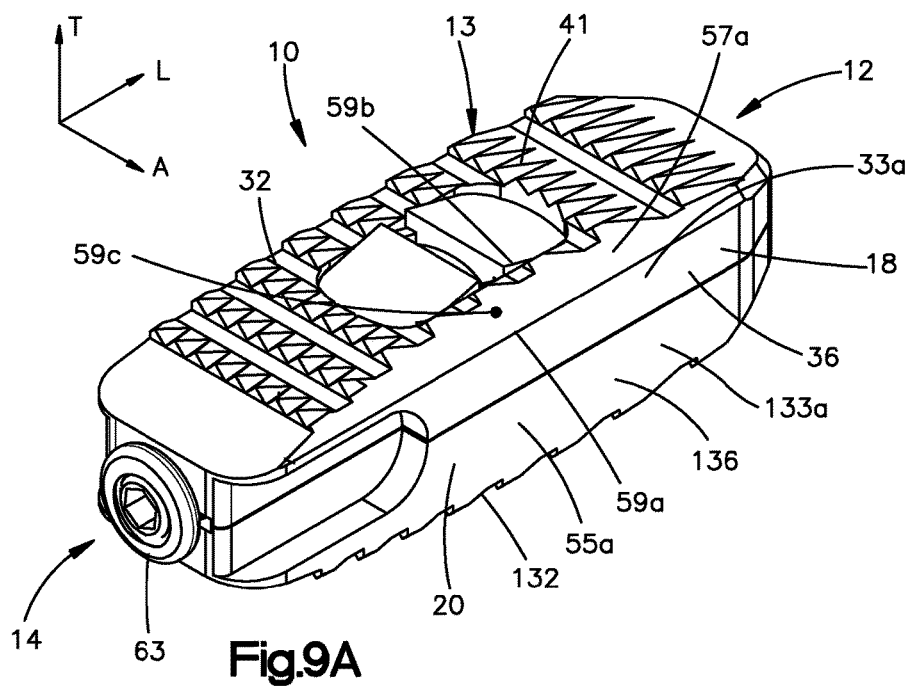
FIG. 9A is a perspective view of an implant similar to the implant illustrated in FIG. 1, but configured to be inserted into an intervertebral space in a first orientation, and subsequently rotated to a second orientation.
Figure 9B:
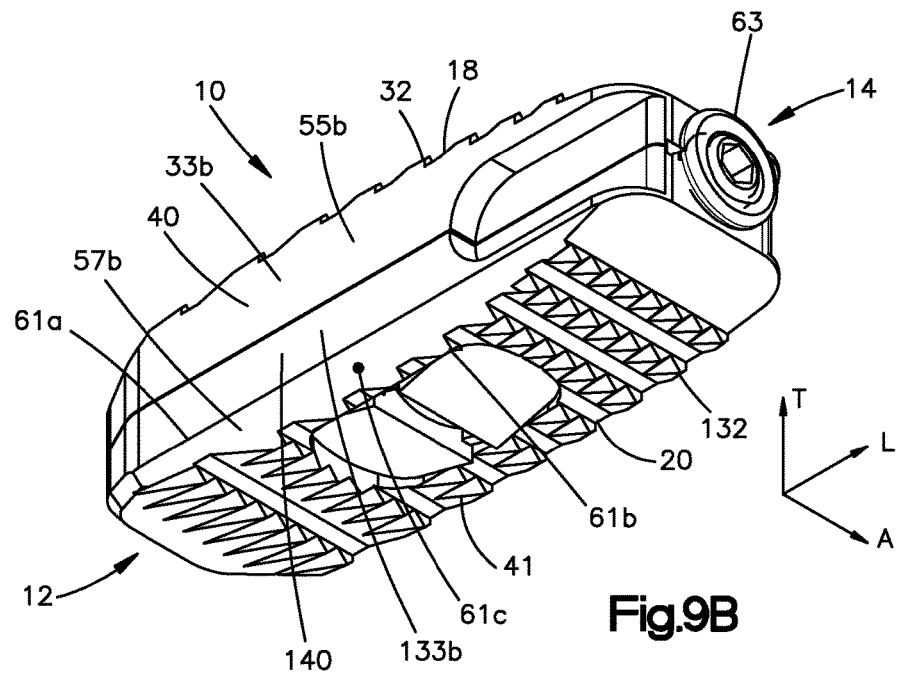
FIG. 9B is another perspective view of the implant illustrated in FIG. 9A.

Referring now to FIGS. 1 and 9A-9B, it should be appreciated that the implant 10 can be configured to be inserted into the intervertebral space 9 in a first orientation, and rotated to a second orientation after insertion into the intervertebral space. The implant body 13 can include the superior plate 18 and the inferior plate 20. Thus, the implant body 13 can further define the first bone contacting surface 32 and the second bone contacting surface 132 that is opposite the first bone contacting surface 32 along the transverse direction T. The implant body 13, and thus the implant 10, can further define a first side surface 55a and a second side surface 55b that is opposite the first side surface 55a along the lateral direction A. The first side surface 55a of the implant body 13 can be defined by the first side surface 33a of the superior plate 18 and the first side surface 133a of the inferior plate 20. Similarly, the second side surface 55b of the implant body 13 can be defined by the second side surface 33b of the superior plate 18 and the second side surface 133b of the inferior plate 20.

The implant body 13, and thus the implant 10, can further include a first intermediate surface 57a that extends from the first side surface 33a, and thus from the first side surface 55a, to the first bone contacting surface 32. Thus, the first intermediate surface 57a can be defined by the superior plate 18. The first intermediate surface 57a can be oblique to each of the first side surface 33a and the first bone contacting surface 32. Thus, the first intermediate surface 57a can be tapered toward the second side surface 33b as it extends along the transverse direction T from the first side surface 33a toward the first bone contacting surface 32. The first intermediate surface 57a can be planar, or can define any suitable curvature or alternative non-planar geometry as desired. For instance, the first intermediate surface 57a can be curved, or can comprise a plurality of segments that are curved segments or planar and extend from each other from the first side surface 55a to the first bone contacting surface 32.

The first intermediate surface 57a can define a first interface 59a with the first side surface 33a, and a second interface 59b with the first bone contacting surface 32. The first and second interfaces 59a and 59b defined by the first intermediate surface 57a can define any suitable shape as desired. For instance, the first interface 59a can be a straight linear interface. The second interface 59b can be a curved interface that extends along a curved path. For instance, the second interface 59b can extend along a curved line. Alternatively, the second interface 59b can extend along a curved path that can be partially defined by the texture 41 of the first end surface 32. In one example, the first bone contacting surface 32 can be curved as it extends along the longitudinal direction L. For instance, the first bone contacting surface 32 can be bowed, and thus can extend out in the transverse direction T as it extends from each of the insertion end 12 and the trailing end 14 toward the other of the insertion end 12 and the trailing end 14. Thus, the first bone contacting surface 32 can define a convex surface.

The first intermediate surface 57a can define a midpoint 59c with respect to the longitudinal direction L. The midpoint can be disposed midway between the opposed ends of the first intermediate surface 57a along the longitudinal direction. In one example, the curved second interface 59b can be symmetrical about the midpoint with respect to the longitudinal direction L. The first intermediate surface 57a can define a distance from the linear first interface 59a to the curved second interface 59b at the midpoint along a direction normal to the first interface 59a. The distance can be a maximum distance of the first intermediate surface 57a along a plane that is defined by the transverse direction T and the lateral direction A. The distance can be within a range of 1 mm and 3 mm. Thus, the distance can be a percentage of the maximum width of the first bone contacting surface 32 along the lateral direction A. The percentage can be within the range of 8% and 38%.

The implant body 13, and thus the implant 10, can further include a second intermediate surface 57b that extends from the second side surface 133b, and thus from the second side surface 55b of the implant 10, to the second bone contacting surface 132. Accordingly, the second intermediate surface 57b can be defined by the inferior plate 20. The second intermediate surface 57b can be oblique to each of the second side surface 133b and the second bone contacting surface 132. Thus, the second intermediate surface 57b can be tapered toward the first side surface 133a as it extends along the transverse direction T from the second side surface 133b toward the second bone contacting surface 132. The second intermediate surface 57b can be planar, or can define any suitable curvature or alternative non-planar geometry as desired. For instance, the second intermediate surface 57b can be curved, or can comprise a plurality of segments that are curved segments or planar and extend from each other from the second side surface 55b to the second bone contacting surface 132.

The second intermediate surface 57b can define a first interface 61a with the second side surface 133b, and a second interface 61b with the second bone contacting surface 132. The first and second interfaces 61a and 61b defined by the second intermediate surface 57b can define any suitable shape as desired. For instance, the first interface 61a can be a straight linear interface. The second interface 61b can be a curved interface. For instance, the second interface 61b can extend along a curved line. Alternatively, the second interface 61b can extend along a curved path that can be partially defined by the texture 41 of the first end surface 32. In one example, the second bone contacting surface 132 can be curved as it extends along the longitudinal direction L. For instance, the second bone contacting surface 132 can be bowed, and thus can extend out in the transverse direction T as it extends from each of the insertion end 12 and the trailing end 14 toward the other of the insertion end 12 and the trailing end 14. Thus, the second bone contacting surface 132 can define a convex surface.

The second intermediate surface 57b can define a midpoint 61c with respect to the longitudinal direction L. The midpoint 61c can be disposed midway between the opposed ends of the second intermediate surface 57b along the longitudinal direction L. In one example, the curved second interface 61b can be symmetrical about the midpoint with respect to the longitudinal direction L. The second intermediate surface 57b can define a distance from the linear interface to the curved interface at the midpoint along a direction normal to the linear interface. The distance can be a maximum distance of the second intermediate surface 57b along a plane that is defined by the transverse direction T and the lateral direction A. The distance can be within a range of 1 mm and 3 mm. Thus, the distance can be a percentage of the maximum width of the first bone contacting surface 32 along the lateral direction A. The percentage can be within the range of 8% and 38%.

It should be appreciated that the first and second intermediate surfaces 57a and 57b can be mirror images of each other. Accordingly, the first and second intermediate surfaces 57a and 57b can be configured to simultaneously contact the superior vertebral body 2 and the inferior vertebral body 4, respectively, as will be described in more detail below. Further, the first and second intermediate surfaces 57a and 57b can be oriented parallel to each other. Thus, the first and second intermediate surfaces 57a and 57b can be planar. Alternatively, the first and second intermediate surfaces 57a and 57b can be curved. For instance, the first and second intermediate surfaces can define convex surfaces. The implant 10 can thus include one of the first and second an intermediate surfaces 57a and 57b at an interface of one side of first and second side surfaces 55a and 55b of the implant 10 and a respective one of the first and second bone contacting surfaces 32 and 132, and the other of the first and second side surfaces 55a and 55b of the implant 10 can extend to the other of the first and second bone contacting surfaces 32 and 132. The first and second intermediate surfaces 57a and 57b can be diagonally opposite each other. The first and second intermediate surfaces 57a and 57b can each be offset in a rotational direction with respect to a midline of the implant 10 oriented in the transverse direction T in a view that is oriented in the insertion direction. For instance, the rotational direction can be a clockwise direction. That is, the first intermediate surface 57a that adjoins the first bone contacting surface 32 can be offset to the right of the midline, and the second intermediate surface 57b that adjoins the second bone contacting surface 132 can be offset to the left of the midline in a view that is oriented in the insertion direction. Thus, the implant 10 can be configured for clockwise rotation in the intervertebral space as described in more detail below. Alternatively, the rotational direction can be a counterclockwise direction. Thus, the implant 10 can be configured for counterclockwise rotation in the intervertebral space as described in more detail below. Alternatively still, the implant can define an intermediate surface at the interface of each of the first and second side surfaces 55a and 55b of the implant 10 and each of the first and second bone contacting surfaces 32 and 132.

Further, at least a portion of each of the first and second intermediate surfaces 57a and 57b can be smooth. That is, the first and second intermediate surfaces 57a and 57b can be devoid of surface texture that would tend to bite into the endplates of the first and second vertebral bodies 2 and 4, respectively. For instance, an entirety of the first intermediate surface 57a can be smooth from the first side surface 133a, and thus from the first side surface 55a of the implant 10, to the first bone contacting surface 32. Further, an entirety of the second intermediate surface 57b can be smooth from the second side surface 133b, and thus from the second side surface 55b of the implant 10, to the second bone contacting surface 132. As described above, the first and second bone contacting surfaces 32 and 132 can be textured. The texture that extends from the first bone contacting surface 32 can be angled in a direction toward the trailing end 14 as it extends out from the first bone contacting surface 32. Similarly, the texture that extends from the second bone contacting surface 132 can be angled in a direction toward the trailing end 14 as it extends out from the first bone contacting surface 32. Thus, the texture can assist in retention of the implant in the intervertebral space and the prevention of backout.

Figure 10A:
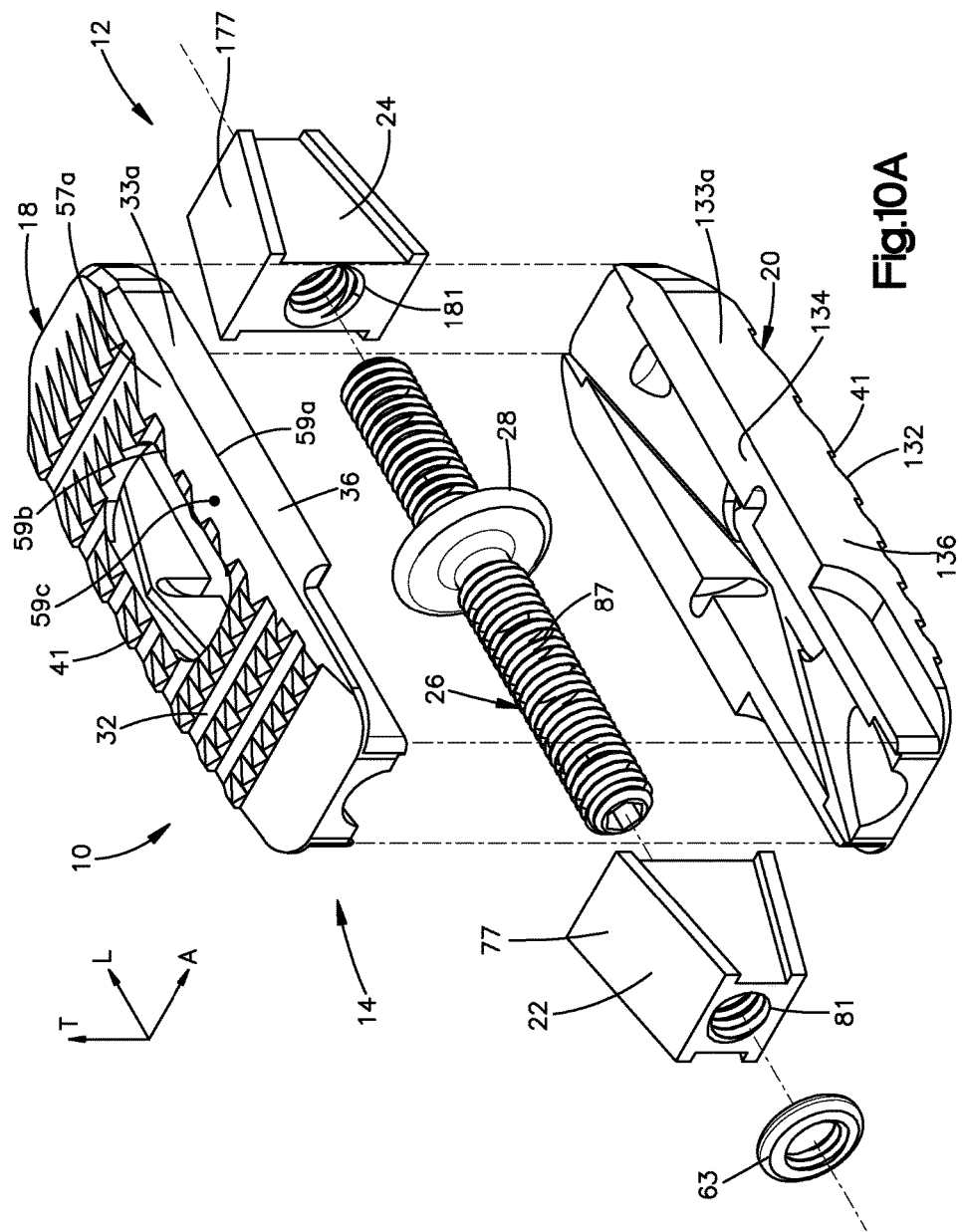
FIG. 10A is an exploded perspective view of the implant shown in FIG. 9A.
Figure 14B:
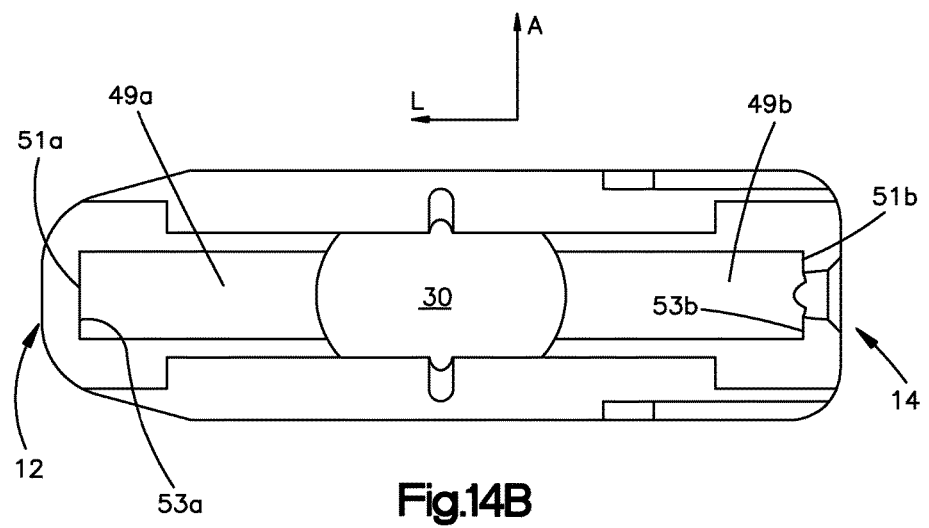
FIG. 14B is an inferior plan view of the plate shown in FIG. 14A.

Referring also to FIGS. 10A-10C, and as described above, the first and second bone contacting surfaces 32 and 132 are movable away from each other from the collapsed configuration to the expanded configuration. For instance, the first and second wedge members 22 and 24 that are coupled between the first and second plates 18 and 20 are configured to translate away from each other so as to cause the implant 10 to move from the contracted configuration to the expanded configuration. The implant 10 can further include a stop member 63 disposed at one or both of the insertion end 12 and the trailing end 14. The stop member 63 is aligned with a respective one of the first and second wedge members 22 and 24 along the longitudinal direction. For instance, the stop member 63 can project radially out with respect to the threaded shaft 87. The stop member 63 is configured and positioned to abut the respective one of the first and second wedge members 22 and 24 when the implant 10 is in the expanded configuration. The abutment between the stop member 63 and the respective one of the first and second wedge members 22 and 24 prevents the first and second wedge members 22 and 24 from moving further away from each other, and thus prevents the first and second plates 18 and 20 from further moving away from each other.

In accordance with one embodiment, the stop member 63 can be threadedly attached to the threaded shaft 87, though it should be appreciated that the stop member 63 can be attached to the threaded shaft 87 in accordance with any suitable alternative embodiment. Alternatively, the stop member 63 can be monolithic with the threaded shaft 87. The stop member 63 can be positioned such that the first and second wedge members 22 and 24 are each disposed between one end of the threaded shaft 87 and the stop member 63. The stop member 63 can be disposed outboard of the implant body with respect to the longitudinal direction L.

Referring now also to FIGS. 11A-11D, a method is provided for inserting the intervertebral implant 10 into the intervertebral space 9 defined between the first vertebral body 2 and the second vertebral body 4. The method can include the steps of inserting the intervertebral implant 10 into the intervertebral space 9, such that the first side surface 55a of the intervertebral implant 10 abuts the first vertebral body 2. For instance, both first side surfaces 33a and 133a can abut the first vertebral body 2. The intervertebral implant 10 can also be inserted into the intervertebral space 9 such that the second side surface 55b of the intervertebral implant 10 abuts the second vertebral body 4. For instance, both second side surfaces 33b and 133b can abut the second vertebral body 4. In one example, the intervertebral implant 10 is inserted into the intervertebral space 9 in the collapsed configuration. The method can further include the step of rotating the intervertebral implant in the direction of rotation about an axis of rotation. For instance, the axis of rotation can be defined by the implant axis 1. The step of rotating can bring the first intermediate surface 57a into contact with the first vertebral body 2, and the second intermediate surface 57b into contact with the second vertebral body 4. The step of rotating can further include the step of substantially removing the first side surface 55a of the implant 10 from abutment with the first vertebral body 2, and can further include the step of substantially removing the second side surface 55b of the implant 10 from abutment with the second vertebral body 4.

The method can then include the step of further rotating the intervertebral implant 10 in the direction of rotation about the axis of rotation such that the first bone contacting surface 32 contacts the first vertebral body 2, and the second bone contacting surface 132 contacts the second vertebral body 4. As described above, the first intermediate surface 57a extends from the first side surface 55a of the implant 10 to the first bone contacting surface 32, and the second intermediate surface 57b extends from the second side surface 55b of the implant 10 to the second bone contacting surface 132. The step of further rotating can include the step of substantially removing the first intermediate surface 57a of the implant 10 from abutment with the first vertebral body 2, and can further include the step of substantially removing the second intermediate surface 57b from abutment with the second vertebral body 4.

The method can further include the step of expanding the intervertebral implant 10 from the collapsed configuration to the expanded configuration, after the further rotating step. When the implant 10 is in the collapsed configuration, the first and second bone contacting surfaces 32 and 132 are spaced from each other a first distance in the transverse direction T.

When the implant 10 is in the expanded configuration, the first and second bone contacting surfaces 32 and 132 are spaced from each other a second distance in the transverse direction T that is greater than the first distance. Further, it is appreciated that the second distance is greater than a distance along the lateral direction A from the first side surface 55a of the implant 10 to the second side surface 55b of the implant 10. Thus, the second distance is greater than a distance along the lateral direction A from the first side surface 33a to the second side surface 33b. Further, the second distance is greater than a distance along the lateral direction A from the first side surface 133a to the second side surface 133b. Further, the second distance is greater than a distance between the first and second intermediate surfaces 57a and 57b when the implant 10 is in the collapsed configuration. It is appreciated that the distance between the first and second intermediate surfaces 57a and 57b is measured along a direction that includes both the lateral direction A and the transverse direction T. In one example, the distance between the first and second intermediate surfaces 57a and 57b can be measured along a line that is normal to the first and second intermediate surfaces. In another example, the distance between the first and second intermediate surfaces 57a and 57b can be measured along a line that extends through the midpoint of each of the first and second intermediate surfaces 57a and 57b. Accordingly, it is appreciated that the first and second vertebral bodies 2 and 4 do not need to be distracted to the second distance prior to insertion of the intervertebral implant 10 into the intervertebral space 9. Thus, the rotatable implant 10 allows the first and second vertebral bodies 2 and 4 to be distracted a distance less than the final expanded height of the implant along the transverse direction T.

As described above with respect to FIGS. 8A-8F, an insertion tool such as the insertion tool 100 or 300 as described above, can include a supporting end that is configured to be received in the indentations 98 and 99 of the implant 10. The supporting end can then be rotated in the direction of rotation so as to correspondingly perform the rotating steps and the further rotating steps. Next, the implant 10 can be expanded from the collapsed configuration to the expanded configuration in the manner described above. For instance, the handle can be rotatably coupled to the handle, such that rotation of the handle in the direction of rotation, causes the supporting end to rotate with the handle. Alternatively, the insertion tool can be constructed such that the supporting end is rotatable with respect to the handle. Thus, the supporting end can be rotated in the direction of rotation with respect to the handle so as to correspondingly cause the rotating and the further rotating steps. It should be further appreciated that the rotating and the further rotating steps can be performed in one continuous rotational motion.

As described above, the threaded shaft 87 is rotatable about a respective axis of rotation in an expansion direction so as to cause the implant 10 to expand from the collapsed configuration to the expanded configuration. The axis of rotation of the threaded shaft 87 can be coincident with the axis of rotation of the implant during the rotating and further rotating steps. Further, the expansion direction can be in the clockwise direction with respect to a view along the longitudinal direction L from the trailing and toward the insertion end of the implant 10. Alternatively, the expansion direction can be in the counterclockwise direction so as to cause the implant 10 to expand from the collapsed configuration to the expanded configuration. As described above, the first and second wedge members 22 and 24 move away from each other as the threaded shaft rotates to expand the implant 10. The threaded shaft 87 can be rotated until one of the first and second wedge members 22 and 24 abuts the stop member 63, which prevents further rotation of the threaded shaft in the expansion direction. The threaded shaft 87 is rotatable in a contraction direction opposite the expansion direction so as to cause the wedge members 22 and 24 to move toward each other, thereby moving the plates 18 and 20 toward each other in a direction from the expanded position toward the collapsed configuration.

Referring to FIGS. 12-14B, in accordance with, the alternative embodiment implant 110, the superior and inferior plates 18 and 20, and specifically the interior include opposing depressions 49, 149 extending from the lumens 30, 131, toward the opposing ends 12, 14 of the implant. The first and second members 22 and 24 may include projecting tabs 120, 121, 122, and 123 (tab 121 not shown) protrude from the inclined surfaces 277 and 278 of the first and second wedge members 22 and 24. Further, the actuation member 226 can have a shorter length compared to actuation member 26 described above. Otherwise, the implant 110 shown in FIGS. 12-14B is similarly configured to implant 10.

Referring the FIGS. 13A-13C, the depressions 79 include a first 49A and a second depression 49B extending from the first and second ramp surfaces 44 and 46 along the transverse direction T. The depressions 49A, 49B define a shoulders 51a, 51b, 53a, 53b, against which a portion the wedge members 22 and 24 shoulder against when the implant is expanded.

Another aspect of the present disclosure is a method of inserting and expanding for inserting an expandable implant into an intervertebral space. The patient the intervertebral space 9 is prepared using familiar techniques. One or more trial implants may be used to determine the appropriate size of the implant 10. Using the tool 100 (FIG. 8A), the expandable implant can be clasped between the tabs 101 and 102. Next, the expandable implant 10 is inserted into the intervertebral space 9 at the appropriate position between the vertebral bodies using a unilateral and/or bilateral posterior approach or an anterior approach. Next, a tool 350 having configured to engage the opening 90 the actuation member 26 can be used to actuate. Rotating the tool 350 and actuation member 26 causes the actuating member 26 to separate the opposed wedge members 22 and 24 along the longitudinal direction L simultaneously, thereby causing the first plate to separate from the second plate along the second direction such that the first plate is parallel to the second plate during the expanding step.

In accordance with an alternative embodiment, the method of insertion and expansion can use a tool 300 shown in FIG. 8C-8F. For instance, the tool 300 can clasp the implant 10 by inserting the tool tabs 312 and 314 into the implant indentations 98 and 99. The rotation member 318 can be slid into engagement with the actuation member 26. The tool 300 can be used to insert the implant into the intervertebral space 9. When the implant 10 is in the appropriate position, the rotation member 318 can be rotated, which rotates the actuation member 26 such that the implant is expanded to the desired expansion height.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant for insertion in an intervertebral space defined between a first vertebral body and a second vertebral body, the implant comprising:
    a first bone contacting surface and a second bone contacting surface opposite the first bone contacting surface along a transverse direction;
    an insertion end and a trailing end opposite the insertion end along a longitudinal direction that is perpendicular to the transverse direction;
    first and second side surfaces opposite each other along a lateral direction that is perpendicular to both the transverse direction and the longitudinal direction;
    a first intermediate surface that extends from the first side surface to the first bone contacting surface, wherein the first intermediate surface defines a respective first interface with the first side surface and a respective second interface with the first bone contacting surface that is inwardly offset from the respective first interface along the lateral direction, and wherein the first intermediate surface is smooth and oblique to each of the first side surface and the first bone contacting surface; and
    a second intermediate surface that extends from the second side surface to the second bone contacting surface, wherein the second intermediate surface defines a respective first interface with the second side surface and a respective second interface with the second bone contacting surface that is inwardly offset from the respective first interface of the second intermediate surface along the lateral direction, wherein the second intermediate surface is smooth and oblique to each of the second side surface and the second bone contacting surface,
    wherein the first and second bone contacting surfaces are movable away from each other from a collapsed configuration to an expanded configuration.

2. The expandable implant as recited in claim 1, wherein the first and second intermediate surfaces are mirror images of each other.

3. The expandable implant as recited in claim 1, wherein the first and second intermediate surfaces are parallel to each other.

4. The expandable implant as recited in claim 1, wherein the first intermediate surface defines a straight linear interface with the first side surface, and a curved interface with the first bone contacting surface.

5. The expandable implant as recited in claim 4, wherein the second intermediate surface defines a straight linear interface with the second side surface, and a curved interface with the second bone contacting surface.

6. The expandable implant as recited in claim 1, wherein the first intermediate surface is tapered toward the second side surface as it extends from the first side surface toward the first bone contacting surface, and the second intermediate surface is tapered toward the first side surface as it extends from the second side surface toward the second bone contacting surface.

7. The expandable implant as recited in claim 1, wherein the first and second bone contacting surfaces are textured.

8. The expandable implant as recited in claim 1, wherein the first and second intermediate surfaces are spaced apart a first distance when the implant is in the collapsed configuration, the first and second bone contacting surfaces are spaced apart a second distance when the implant is in the expanded configuration, and the second distance is greater than the first distance.

9. The expandable implant as recited in claim 1, further comprising:
    first and second plates that define the first and second bone contacting surfaces, respectively;
    a first wedge member and a second wedge member spaced from the first wedge member along the longitudinal direction, the first and second wedge members coupled between the first and second plates, wherein the first and second wedge members are configured to translate away from each other so as to cause the implant to move from the contracted configuration to the expanded configuration; and
    a stop member disposed at one of the insertion and trailing ends, the stop member configured to abut a respective one of the first and second wedge members so as to prevent the first and second plates from further moving away from each other.

10. The expandable implant as recited in claim 9, further comprising an actuation member that includes a threaded shaft that is threadedly coupled to each of the first and second wedge members, wherein rotation of the threaded shaft causes the first and second wedge members to translate along the longitudinal direction, wherein the stop member projects radially out with respect to the threaded shaft.

11. The expandable implant as recited in claim 10, wherein the stop member is threaded onto the threaded shaft.

12. The expandable implant as recited in claim 1, further comprising:
    first and second plates that define the first and second bone contacting surfaces, respectively,
    wherein the first side surface of the implant includes a first side surface of the first plate and a first side surface of the second plate.

13. The expandable implant as recited in claim 12, wherein the first intermediate surface extends from the first side surface of the first plate to the first bone contacting surface.

14. The expandable implant as recited in claim 13, wherein the first side surface of the first plate and the first side surface of the second plate abut each other in the collapsed configuration, and the first side surface of the first plate and the first side surface of the second plate are spaced from each other along the transverse direction in the expanded configuration.

15. The expandable implant as recited in claim 14, wherein the first side surface of the second plate extends from the second bone contacting surface toward the first side surface of the first plate.

16. The expandable implant as recited in claim 14, wherein the second side surface of the implant includes a second side surface of the first plate and a second side surface of the second plate.

17. The expandable implant as recited in claim 16, wherein the second intermediate surface extends from the second side surface of the second plate to the second bone contacting surface.

18. The expandable implant as recited in claim 17, wherein the second side surface of the first plate and the second side surface of the second plate abut each other in the collapsed configuration, and the second side surface of the first plate and the second side surface of the second plate are spaced from each other along the transverse direction in the expanded configuration.

19. The expandable implant as recited in claim 18, wherein the second side surface of the first plate extends from the first bone contacting surface toward the second side surface of the second plate.

20. The expandable implant as recited in claim 1, wherein the second interface of the first intermediate surface and the second interface of the second intermediate surface are disposed between the first interface of the first intermediate surface and the first interface of the second intermediate surface with respect to the lateral direction.

21. The expandable implant as recited in claim 1, wherein the first intermediate surface is oblique to each of the first side surface and the first bone contacting surface from the respective first interface to the respective second interface, and the second intermediate surface is oblique to each of the second side surface and the second bone contacting surface from the respective first interface to the respective second interface.

* * * * *